US008519198B2

(12) United States Patent
Gilbeau

(10) Patent No.: US 8,519,198 B2
(45) Date of Patent: Aug. 27, 2013

(54) METHOD FOR MAKING AN EPOXIDE

(75) Inventor: Patrick Gilbeau, Braine-le-Comte (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 13/427,082

(22) Filed: Mar. 22, 2012

(65) Prior Publication Data

US 2012/0199786 A1 Aug. 9, 2012

Related U.S. Application Data

(63) Continuation of application No. 11/914,879, filed as application No. PCT/EP2006/062437 on May 19, 2006, now Pat. No. 8,173,823.

(60) Provisional application No. 60/734,659, filed on Nov. 8, 2005, provisional application No. 60/734,627, filed on Nov. 8, 2005, provisional application No. 60/734,657, filed on Nov. 8, 2005, provisional application No. 60/734,658, filed on Nov. 8, 2005, provisional application No. 60/734,635, filed on Nov. 8, 2005, provisional application No. 60/734,634, filed on Nov. 8, 2005, provisional application No. 60/734,637, filed on Nov. 8, 2005, provisional application No. 60/734,636, filed on Nov. 8, 2005.

(30) Foreign Application Priority Data

May 20, 2005 (EP) .................................... 05104321
May 20, 2005 (FR) .................................... 05 05120

(51) Int. Cl.
*C07C 31/10* (2006.01)
*C07C 29/60* (2006.01)

(52) U.S. Cl.
USPC .......................................... 568/841; 514/724

(58) Field of Classification Search
USPC .......................................... 514/724; 568/841
See application file for complete search history.

(56) References Cited

U.S. PATENT DOCUMENTS

| | | |
|---|---|---|
| 280,893 A | 7/1883 | Baujard |
| 865,727 A | 9/1907 | Queneau |
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,505,735 A | 4/1950 | Halbedel |
| 2,726,072 A | 12/1955 | Hermann |
| 2,733,195 A | 1/1956 | Miller |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,052,612 A | 9/1962 | Henegar et al. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,104,434 A | 8/1978 | Johnson |
| 4,127,594 A | 11/1978 | Anderson et al. |
| 4,173,710 A | 11/1979 | Boulet et al. |

(Continued)

FOREIGN PATENT DOCUMENTS

| | | |
|---|---|---|
| BE | 422877 | 8/1937 |
| CA | 1119320 | 8/2003 |

(Continued)

OTHER PUBLICATIONS

Wu, Guoying, et al., "Preparation of Biodiesel and Glycerol by Methyl Esterification of Cottonseed Oil," China Oil and Fat, (2003), vol. 28, Iss. 4, 70-73, pp. 1-9.
Zhu Shiyong, "Production and Prospects of the World's Natural Glycerin," Cereals and Oils, (1997), Issue 01, 33-38, pp. 1-15.
Arthur J. Hill et al, "A Synthesis of Beta-Chloro-Ally Chloride," Journal American Chemical Society, 1922, 44(11), 2582-2595.
Physical and Chemical Dictionary (5th Edition), Feb. 20, 1998 (with attached English translation of cited excerpt).
Encyclopaedia CHIMICA, No. 8, 1$^{st}$ Edition, Feb. 28, 1962 1-1, (with attached English translation of cited excerpt).
Encyclopaedia CHIMICA, No. 2, 1$^{st}$ Edition, Jun. 30, 1960, 1-2, (with attached English translation of cited excerpt).
Klaus Gottlieb, et al., "Glycerine—A Sustainable Raw Material," Chem. Ing. Tech. 66 (1994) Nr.1, S, 64-66 (with attached English translation).

(Continued)

*Primary Examiner* — Elvis O Price
(74) *Attorney, Agent, or Firm* — Oblon, Spivak, McClelland, Maier & Neustadt, L.L.P.

(57) ABSTRACT

A mixture of compounds containing 1,3-dichloropropan-2-ol, 2,3-dichloropropan-1-ol, and a halogenated ketone, where the halogenated ketone content of the mixture is at least 0.0001% by weight and less than or equal to 0.1% by weight relative to the 1,3-dichloropropan-2-ol and 2,3-dichloropropan-1-ol.

17 Claims, 4 Drawing Sheets

(56) References Cited

U.S. PATENT DOCUMENTS

Figure 1:
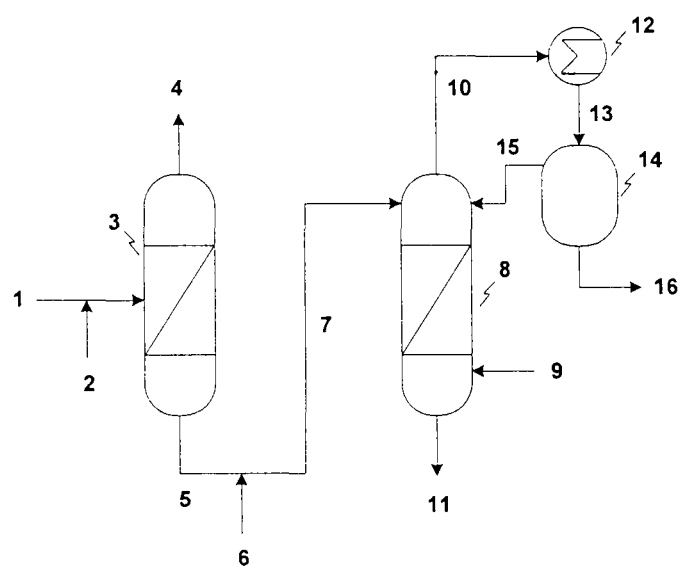

| | | | |
|---|---|---|---|
| 4,197,399 A | 4/1980 | Noel et al. |
| 4,220,529 A | 9/1980 | Daude-Lagrave |
| 4,240,885 A | 12/1980 | Suciu et al. |
| 4,255,470 A | 3/1981 | Cohen et al. |
| 4,322,367 A | 3/1982 | Silvis |
| 4,390,680 A | 6/1983 | Nelson |
| 4,405,465 A | 9/1983 | Moore et al. |
| 4,415,460 A | 11/1983 | Suciu et al. |
| 4,464,517 A | 8/1984 | Makino et al. |
| 4,499,255 A | 2/1985 | Wang et al. |
| 4,595,469 A | 6/1986 | Foller |
| 4,609,751 A | 9/1986 | Hajjar |
| 4,634,784 A | 1/1987 | Nagato et al. |
| 4,655,879 A | 4/1987 | Brockmann et al. |
| 4,898,644 A | 2/1990 | Van Horn |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,169,964 A | 12/1992 | Jakobson et al. |
| 5,200,163 A | 4/1993 | Henkelmann et al. |
| 5,278,260 A | 1/1994 | Schaffner et al. |
| 5,286,354 A | 2/1994 | Bard et al. |
| 5,344,945 A | 9/1994 | Grunchard |
| 5,359,094 A | 10/1994 | Teles et al. |
| 5,393,428 A | 2/1995 | Dilla et al. |
| 5,445,741 A | 8/1995 | Dilla et al. |
| 5,478,472 A | 12/1995 | Dilla et al. |
| 5,486,627 A | 1/1996 | Quarderer, Jr. et al. |
| 5,532,389 A | 7/1996 | Trent et al. |
| 5,567,359 A | 10/1996 | Cassidy et al. |
| 5,578,740 A | 11/1996 | Au et al. |
| 5,710,350 A | 1/1998 | Jeromin et al. |
| 5,731,476 A | 3/1998 | Shawl et al. |
| 5,744,655 A | 4/1998 | Thomas et al. |
| 5,766,270 A | 6/1998 | Neuman et al. |
| 5,779,915 A | 7/1998 | Becker et al. |
| 5,908,946 A | 6/1999 | Stern et al. |
| 5,955,043 A | 9/1999 | Neuman et al. |
| 5,993,974 A | 11/1999 | Fukushima et al. |
| 6,103,092 A | 8/2000 | Silva |
| 6,111,153 A | 8/2000 | Crow et al. |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 | 9/2001 | Strebelle et al. |
| 6,288,287 B2 | 9/2001 | Ueoka et al. |
| 6,350,888 B1 | 2/2002 | Strebelle et al. |
| 6,350,922 B1 | 2/2002 | Vosejpka et al. |
| 6,428,759 B1 | 8/2002 | Smith et al. |
| 6,589,497 B2 | 7/2003 | Smith |
| 6,719,957 B2 | 4/2004 | Brady, Jr. et al. |
| 6,740,633 B2 | 5/2004 | Norenberg et al. |
| 6,960,673 B2 | 11/2005 | Brunner et al. |
| 7,126,032 B1 | 10/2006 | Aiken |
| 7,128,890 B2 | 10/2006 | Ollivier |
| 7,453,008 B2 | 11/2008 | Ko et al. |
| 7,557,253 B2 | 7/2009 | Gilbeau |
| 7,584,629 B2 | 9/2009 | Sohn et al. |
| 7,615,670 B2 | 11/2009 | Gilbeau |
| 7,619,056 B2 | 11/2009 | East et al. |
| 7,893,193 B2 | 2/2011 | Krafft et al. |
| 7,906,691 B2 | 3/2011 | Krafft et al. |
| 7,906,692 B2 | 3/2011 | Krafft et al. |
| 7,939,696 B2 | 5/2011 | Krafft et al. |
| 8,067,645 B2 | 11/2011 | Gilbeau et al. |
| 8,106,245 B2 | 1/2012 | Krafft et al. |
| 8,106,246 B2 | 1/2012 | Krafft et al. |
| 8,124,814 B2 | 2/2012 | Krafft et al. |
| 8,173,823 B2 | 5/2012 | Gilbeau |
| 8,197,665 B2 | 6/2012 | Krafft et al. |
| 8,258,350 B2 | 9/2012 | Krafft et al. |
| 8,273,923 B2 | 9/2012 | Borremans |
| 8,314,205 B2 | 11/2012 | Gilbeau et al. |
| 8,344,185 B2 | 1/2013 | Krafft |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0047781 A1 | 3/2004 | Becenel, Jr. |
| 2004/0150123 A1 | 8/2004 | Strofer et al. |
| 2004/0179987 A1 | 9/2004 | Oku et al. |
| 2004/0232007 A1 | 11/2004 | Carson et al. |
| 2005/0115901 A1 | 6/2005 | Heuser et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0251831 A1 | 11/2007 | Kaczur et al. |
| 2007/0293707 A1 | 12/2007 | Wolfert et al. |
| 2008/0021209 A1 | 1/2008 | East et al. |
| 2008/0053836 A1 | 3/2008 | Bulan et al. |
| 2008/0146753 A1 | 6/2008 | Woike et al. |
| 2008/0154050 A1 | 6/2008 | Gilbeau |
| 2008/0194850 A1 | 8/2008 | Krafft et al. |
| 2008/0194851 A1 | 8/2008 | Gilbeau |
| 2008/0200701 A1 | 8/2008 | Krafft et al. |
| 2008/0214848 A1 | 9/2008 | Krafft et al. |
| 2008/0281132 A1 | 11/2008 | Krafft et al. |
| 2009/0022653 A1 | 1/2009 | Strebelle et al. |
| 2009/0173636 A1 | 7/2009 | Ooms et al. |
| 2009/0198041 A1 | 8/2009 | Krafft et al. |
| 2009/0270588 A1 | 10/2009 | Krafft et al. |
| 2009/0275726 A1 | 11/2009 | Krafft et al. |
| 2010/0029959 A1 | 2/2010 | Fan et al. |
| 2010/0032617 A1 | 2/2010 | Gilbeau et al. |
| 2010/0105964 A1 | 4/2010 | Krafft et al. |
| 2010/0168379 A1 | 7/2010 | Krafft et al. |
| 2010/0179300 A1 | 7/2010 | Boulos et al. |
| 2010/0179302 A1 | 7/2010 | Krafft et al. |
| 2010/0212540 A1 | 8/2010 | Bobet et al. |
| 2010/0294727 A1 | 11/2010 | Gilbeau et al. |
| 2010/0305271 A1 | 12/2010 | Mentink et al. |
| 2010/0311874 A1 | 12/2010 | Mentink et al. |
| 2010/0311905 A1 | 12/2010 | Mentink et al. |
| 2011/0028683 A1 | 2/2011 | Gilbeau et al. |
| 2011/0086949 A1 | 4/2011 | Mentink et al. |
| 2011/0118390 A1 | 5/2011 | Feron et al. |
| 2011/0152545 A1 | 6/2011 | Balthasart et al. |
| 2011/0166369 A1 | 7/2011 | Krafft et al. |
| 2011/0195148 A1 | 8/2011 | Mentink et al. |
| 2011/0237773 A1 | 9/2011 | Gilbeau |
| 2012/0010420 A1 | 1/2012 | Gilbeau et al. |
| 2012/0199493 A1 | 8/2012 | Krafft et al. |
| 2012/0199786 A1 | 8/2012 | Gilbeau |

FOREIGN PATENT DOCUMENTS

| | | |
|---|---|---|
| CN | 1135533 | 11/1996 |
| CN | 1296003 | 5/2001 |
| CN | 101041421 | 9/2007 |
| DE | 58396 | 8/1891 |
| DE | 197 308 | 11/1906 |
| DE | 238 341 | 3/1908 |
| DE | 869 193 | 3/1953 |
| DE | 1 041 488 | 10/1958 |
| DE | 1 075 103 | 2/1960 |
| DE | 1 226 554 | 10/1966 |
| DE | 2 241 393 | 2/1974 |
| DE | 25 21 813 | 12/1975 |
| DE | 30 03 819 | 8/1981 |
| DE | 216 471 | 6/1983 |
| DE | 32 43 617 | 5/1984 |
| DE | 37 21 003 | 6/1987 |
| DE | 43 02 306 | 8/1994 |
| DE | 43 35 311 | 4/1995 |
| DE | 102 03 914 | 1/2002 |
| DE | 102 54 709 | 6/2004 |
| DE | 238341 | 3/2008 |
| DE | 197 309 | 4/2008 |
| EP | 180 668 | 1/1906 |
| EP | 0 296 341 | 12/1988 |
| EP | 0 317 184 | 5/1989 |

| | | | | | | |
|---|---|---|---|---|---|---|
| EP | 0 317 185 | 5/1989 | | JP | 50 037714 | 4/1975 |
| EP | 0 347 618 | 12/1989 | | JP | 50-062909 | 5/1975 |
| EP | 0 421 379 | 4/1991 | | JP | 55-041858 | 3/1980 |
| EP | 0 452 265 | 10/1991 | | JP | 56-29572 | 3/1981 |
| EP | 0 518 765 | 12/1992 | | JP | 56-99432 | 8/1981 |
| EP | 0 522 382 | 1/1993 | | JP | 61-112066 | 5/1986 |
| EP | 0 535 949 | 4/1993 | | JP | 61-236749 | 10/1986 |
| EP | 0 563 720 | 10/1993 | | JP | 62-242638 | 10/1987 |
| EP | 0 568 389 | 11/1993 | | JP | 63-195288 | 8/1988 |
| EP | 0 582 201 | 2/1994 | | JP | 2-137704 | 5/1990 |
| EP | 0 618 170 | 10/1994 | | JP | 03-014527 | 1/1991 |
| EP | 0 916 624 | 5/1999 | | JP | 3-223267 | 10/1991 |
| EP | 0 919 551 | 6/1999 | | JP | 03-223267 | 10/1991 |
| EP | 0 774 450 | 2/2000 | | JP | 04-089440 | 3/1992 |
| EP | 0 979 671 | 2/2000 | | JP | 04-217637 | 8/1992 |
| EP | 1 059 278 | 12/2000 | | JP | 6-25196 | 4/1994 |
| EP | 1 106 237 | 6/2001 | | JP | 6-184024 | 7/1994 |
| EP | 1 153 887 | 11/2001 | | JP | 06-321852 | 11/1994 |
| EP | 1 163 946 | 12/2001 | | JP | 8-59593 | 3/1996 |
| EP | 1 231 189 | 8/2002 | | JP | 09-299953 | 11/1997 |
| EP | 1 298 154 | 4/2003 | | JP | 10-139700 | 5/1998 |
| EP | 0 561 441 | 9/2003 | | JP | 10-218810 | 8/1998 |
| EP | 1 411 027 | 4/2004 | | JP | 2000-344692 | 12/2000 |
| EP | 1 752 435 | 2/2007 | | JP | 2001-037469 | 2/2001 |
| EP | 1 752 436 | 2/2007 | | JP | 2001-213827 | 8/2001 |
| EP | 1 760 060 | 3/2007 | | JP | 2001-261308 | 9/2001 |
| EP | 1 762 556 | 3/2007 | | JP | 2001-1261581 | 9/2001 |
| EP | 1 770 081 | 4/2007 | | JP | 2002-02033 | 1/2002 |
| EP | 1 772 446 | 4/2007 | | JP | 2002-038195 | 2/2002 |
| EP | 1 775 278 | 4/2007 | | JP | 2002-265986 | 9/2002 |
| EP | 2 085 364 | 8/2009 | | JP | 2002-363153 | 12/2002 |
| FR | 1 056 360 | 2/1954 | | JP | 2003-81891 | 3/2003 |
| FR | 1 306 231 | 10/1961 | | JP | 2003-89680 | 3/2003 |
| FR | 1 417 388 | 10/1964 | | JP | 2005-007841 | 1/2005 |
| FR | 1 476 073 | 4/1966 | | JP | 2005-097177 | 4/2005 |
| FR | 1 577 792 | 8/1968 | | JP | 76021635 | 4/2005 |
| FR | 2 180 138 | 5/1973 | | JP | 2005-154292 | 6/2005 |
| FR | 2 217 372 | 2/1974 | | JP | 2007-008898 | 1/2007 |
| FR | 2 565 229 | 12/1985 | | JP | 2009-263338 | 11/2009 |
| FR | 2 752 242 | 2/1998 | | KR | 900006513 | 11/1987 |
| FR | 2 862 644 | 5/2005 | | KR | 2003-29740 | 5/2003 |
| FR | 2 868 419 | 10/2005 | | KR | 10-0514819 | 11/2004 |
| FR | 2 869 612 | 11/2005 | | SU | 123153 | 1/1959 |
| FR | 2 869 613 | 11/2005 | | SU | 1125226 | 11/1984 |
| FR | 2 872 504 | 1/2006 | | SU | 1159716 | 6/1985 |
| FR | 2 881 732 | 8/2006 | | SU | 1685969 | 10/1991 |
| FR | 2 885 903 | 11/2006 | | WO | WO 95/14635 | 6/1995 |
| FR | 2 912 743 | 8/2008 | | WO | WO 95/14639 | 6/1995 |
| FR | 2 913 683 | 9/2008 | | WO | WO 96/07617 | 3/1996 |
| FR | 2 917 411 | 12/2008 | | WO | WO 96/15980 | 5/1996 |
| FR | 2 918 058 | 1/2009 | | WO | WO 97/48667 | 12/1997 |
| FR | 2 925 045 | 6/2009 | | WO | WO 98/37024 | 8/1998 |
| FR | 2 927 083 | 8/2009 | | WO | WO 99/14208 | 3/1999 |
| FR | 2 929 611 | 10/2009 | | WO | WO 99/32397 | 7/1999 |
| FR | 2 935 699 | 3/2010 | | WO | WO 2000/24674 | 5/2000 |
| FR | 2 935 968 | 3/2010 | | WO | WO 01/41919 | 6/2001 |
| GB | 14 767 | 0/1914 | | WO | WO 01/43762 | 6/2001 |
| GB | 404 938 | 7/1932 | | WO | WO 01/86220 | 11/2001 |
| GB | 406345 | 8/1932 | | WO | WO 02/26672 | 4/2002 |
| GB | 467 481 | 9/1935 | | WO | WO 03/064357 | 8/2003 |
| GB | 541357 | 11/1941 | | WO | WO 2004/056758 | 7/2004 |
| GB | 724222 | 6/1952 | | WO | WO 2005/021476 | 3/2005 |
| GB | 679 536 | 9/1952 | | WO | WO 2005/054167 | 6/2005 |
| GB | 736641 | 7/1953 | | WO | WO 2005/075189 | 8/2005 |
| GB | 758665 | 10/1954 | | WO | WO 2005/097722 | 10/2005 |
| GB | 799 567 | 8/1958 | | WO | WO 2005/115954 | 12/2005 |
| GB | 1046521 | 1/1964 | | WO | WO 2005/116004 | 12/2005 |
| GB | 1083594 | 11/1964 | | WO | WO 2006/020234 | 2/2006 |
| GB | 984446 | 2/1965 | | WO | WO 2006/100311 | 9/2006 |
| GB | 984 633 | 3/1965 | | WO | WO 2006/100312 | 9/2006 |
| GB | 1 387 668 | 3/1972 | | WO | WO 2006/100313 | 9/2006 |
| GB | 1286893 | 8/1972 | | WO | WO 2006/100314 | 9/2006 |
| GB | 1 493 538 | 4/1975 | | WO | WO 2006/100315 | 9/2006 |
| GB | 1 414 976 | 11/1975 | | WO | WO 2006/100316 | 9/2006 |
| GB | 2 173 496 | 10/1986 | | WO | WO 2006/100317 | 9/2006 |
| GB | 702143 | 10/1990 | | WO | WO 2006/100318 | 9/2006 |
| GB | 2 336 584 | 10/1999 | | WO | WO 2006/100319 | 9/2006 |
| HU | 2002-003023 | 3/2004 | | WO | WO 2006/100320 | 9/2006 |
| JP | 39-27230 | 11/1928 | | WO | WO 2006/106153 | 10/2006 |

| | | |
|---|---|---|
| WO | WO 2006/106154 | 10/2006 |
| WO | WO 2006/106155 | 10/2006 |
| WO | WO 2007/005405 | 5/2007 |
| WO | WO 2007/054505 | 5/2007 |
| WO | WO 2007/144335 | 12/2007 |
| WO | WO 2008/101866 | 8/2008 |
| WO | WO 2008/107468 | 9/2008 |
| WO | WO 2008/110588 | 9/2008 |
| WO | WO 2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO 2009/000773 | 12/2008 |
| WO | WO 2009/016149 | 2/2009 |
| WO | WO 2009/026212 | 2/2009 |
| WO | WO 2009/043796 | 4/2009 |
| WO | WO 2009/077528 | 6/2009 |
| WO | WO 2009/095429 | 8/2009 |
| WO | WO 2009/095617 | 8/2009 |
| WO | WO 2009/095618 | 8/2009 |
| WO | WO 2009/095622 | 8/2009 |
| WO | WO 2009/121853 | 10/2009 |
| WO | WO 2009/150385 | 12/2009 |
| WO | WO 2010/010282 | 1/2010 |
| WO | WO 2010/029039 | 3/2010 |
| WO | WO 2010/029153 | 3/2010 |
| WO | WO 2010/043813 | 4/2010 |
| WO | WO 2010/066660 | 6/2010 |
| WO | WO 2010/136725 | 12/2010 |
| WO | WO 2011/054769 | 5/2011 |
| WO | WO 2011/054770 | 5/2011 |
| WO | WO 2012/016872 | 2/2012 |
| WO | WO 2012/025468 | 3/2012 |
| WO | WO 2012/041816 | 4/2012 |
| WO | WO 2012/056005 | 5/2012 |

OTHER PUBLICATIONS

Wissenschaft & Technik, Mar. 1995, pp. 139-142 (no translation).
Milchert et al., "Dehydrochlorination of Glycerol Dichlorohydrin to Epichlorohydrin," Chem. Papers, 49 (3) 133-136 (1995).
M. Demarquay, "De La Glycerine," Librairie de la Faculté de Médecine, Paris 1863 (no translation).
Perry's Chemical Engineers Handbook, Sixth Edition, Mc Graw Hill Inc., 1984, Section 14 (pp. 14-1-14-40).
Perry's Chemical Engineers Handbook, Sixth Edition, Mc Graw Hill Inc., 1984, Section 22-32 to 22-37.
U.S. Appl. No. 13/818,753, filed Feb. 25, 2013, Gilbeau, et al.
U.S. Appl. No. 13/878,429, filed Apr. 9, 2013, Balthasart, et al.
New Experimental Chemical Course 1, Basic Operation I, Section 4, Separation and Purification, pp. 251-252, Issued Sep. 20, 1975 (with English Translation).
Copyright Mar. 1992, Advanced Organic Chemistry, 4$^{th}$ Ed., pp. 889, 908 and 937.
Yong, K.C., et al., "Refining of Crude Glycerine Recovered from Glycerol Residue by Simple Vacuum Distillation," Journal of Oil Palm Research, vol. 13, No. 2, Dec. 2001, pp. 39-44.
Friedel et Silva, Bulletin de la Société Chimique de Paris, Année 1873, 1er semestre—Nouvelle Série—Tome XIX, p. 98.
I.S. Neuberg, Biochemische Zeitshrift, 1930, vol. 221, pp. 492-493.
Krausz Ann. De Chimie, 12e série, t. 4 Nov.-Dec. 1949, pp. 811-931.
Glycerin : An overview, Soap and Detergent Association. Copyright 1990 by the Soap and Detergent Association.
Chemical and Engineering News, 1948, 26 (38), pp. 2770-2771.
Fairbourn et al., "The Partial Esterification of Polyhydric Alcohols. Part XII. The Function of Ethylene-oxide Rings," J. Chem. Soc. 1932, pp. 1965-1972, Received, Apr. 6, 1932.
Clarke et al., Organic Syntheses, Coll., vol. 1, p. 233, (1941); vol. 3, p. 47, ( 1923).
Braun, Organic Syntheses, Coll., vol. 2, p. 256, (1943); vol. 6, p. 30, (1936).
Conant et al. Organic Syntheses, Coll., vol. 1, p. 292, (1941); vol. 2, p. 29, (1922).
Bull. Soc. Chim. Fr. (1943), 10, pp. 52-58, with English Translation.
Schröder et al. "Glycerol as a By-Product of Biodiesel Production in Diets for Ruminants," Institute of Animal Nutrition, Physiology and Metabolism, University of Kiel, 24098 Kiel.
"Chemical Properties and Derivatives of Glycerol", (1965), published by Glycerine Producers' Association in New York, pp. 1-20.
G.W. Busby and D.E. Gosvenor, "The Purification of Glycerin by Ion-Exchange," The Journal of the American Oil Chemists' Society, vol. 29, No. 8, pp. 318-320 (1952).
L.L. Lamborn, "Modern Soaps, Candles and Glycerin," D. Van NOstrand Company, London, third edition 1918, pp. 542-550, 573-574.
G. Knothe, "Historical perspectives on vegetable oil-based diesel fuels", Inform, vol. 12, Nov. 2001. pp. 1103-1107.
U. Schuchardt et al., "Transesterification of Vegetable Oils: a Review," J. Braz. Chem. Soc., vol. 9, No. 1, 199-210, 1998.
S. Claude, "Research of new outlets for glycerol—recent developemnts in France," Fett/Lipid 101 (1999), Nr. 3, S 101-104.
C.B. Prakash, "A critical review of Biodiesel as a Transportation Fuel in Canada," for the Transportation Systems Branch Air Pollution Prevention Directorate Enviornment Canada, Mar. 25, 1998, pp. 1-104.
H. Fukuda et al., "Biodiesel Fuel Production by transesterification of Oils", Journal of Bioscience and Bioengineering, vol. 92, No. 5, pp. 405-416 (2001).
Kaszonyi A. et al., "Bioglycerol a new platform chemical", in 44th International Petroleum Conference, 2009, 8 p., Bratislava, Slovak Republic.
Williamson R. et al., "DE-FC36-03GO1300 Final Report: Continuous Isosorbide Production from Sorbitol using Solid Acid Catalysis", 2006, 9 p., DOE Award for Iowa Corn Promotion Board.
Malhotra S. V. et al., "Applications of Corn-Based Chemistry", in The Bridge Publication of the National Academy of Engineering, 2007, V 34, No. 4, 8 p.
Jaffe M. et al., "Corn (Sugars) Based Chemistries for the Polymer Industry", in ANTEC 2009, 67th Annual Technical Conf., Proceed., Society of Plastic Engineers, Jun. 22-24, Mc Cormick, Place West Chigaco, Illinois.
Anon., "Iowa Corn Promotion Board, NJIT to License Breakthrough, Safe Bio-Plastic Alternative", New Jersey Science & Technology University press release, Aug. 6, 2008.
Anon., "NJIT Patent May Be Able to Replace BPA; Make Consumer Products Safer", New Jersey Science & Technology University press release, Feb. 4, 2010.
Fenouillot F. et al, "Polymers from renewable 1,4:3,6-dianhydrohexitols (isosorbide isomannide and isoidide): A Review", in Progress in Polymer Science, 2010, V 35, N 5, p. 578-622.
U.S. Appl. No. 13/832,363, filed Mar. 15, 2013, Krafft, et al.
U.S. Appl. No. 13/876,003, filed Mar. 26, 2013, Gilbeau, et al.
Trent et al., "Reactive Stripping in a Rotating Packed Bed for the Production of Hypochlorous Acid", BHR Group, Conference Series Publication (1999), 38 (Process Intensification for the Chemical Industry), 217-231.
M. Vajda et al., Membrane-Based Extraction Joined With Membrane-Based Stripping in a Circulating Arrangement II. Extraction of Organic Acids, Chemical Papers, (2003), 57(1), 3-10.
U.S. Appl. No. 60/560,676, filed Apr. 8, 2004, Gilbeau, et al.
U.S. Appl. No. 60/734,659, filed Nov. 8, 2005, Krafft, et al.
U.S. Appl. No. 60/734,627, filed Nov. 8, 2005, Krafft, et al.
U.S. Appl. No. 60/734,657, filed Nov. 8, 2005, Krafft, et al.
U.S. Appl. No. 60/734,658, filed Nov. 8, 2005, Gilbeau, et al.
U.S. Appl. No. 60/734,635, filed Nov. 8, 2005, Krafft, et al.
U.S. Appl. No. 60/734,634, filed Nov. 8, 2005, Krafft, et al.
U.S. Appl. No. 60/734,637, filed Nov. 8, 2005, Krafft, et al.
U.S. Appl. No. 60/734,636, filed Nov. 8, 2005, Krafft, et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007.
U.S. Appl. No. 13/623,979, filed Sep. 21, 2012, Gilbeau.
U.S. Appl. No. 13/755,236, filed Jan. 31, 2013, Krafft, et al.
U.S. Appl. No. 13/709,218, filed Dec. 10, 2012, Boulos, et al.
U.S. Appl. No. 13/813,348, filed Jan. 30, 2013, Gilbeau, et al.

Gibson, "The Preparation, Properties, and Uses of Glycerol Derivatives. Part III. The Chlorohydrins", Chemistry and Industry, Chemical Society, pp. 949-975 (1931).
Carre et al., "La Transformation Des Alcools Polyatomiques En Mono-Et En Polychlorhydrines Au Moyen Du Chlorure De Thionyle", Bull. Soc. Chim. Fr., No. 49, pp. 1150-1154 (1931).
Fauconnier, "Preparation De L'Epichlorohydrine", Bull. Soc. Chim. Fr. No. 50, pp. 212-214, 1888.
"Industrially Important Epoxides", Ullmann's Encylopedia of Industrial Chemistry, 5. Ed., vol. A9, pp. 539-540.
Bonner et al., "The Composition of Constant Boiling Hydrochloric Acid at Pressures of 50 to 1220 Millimeters", Journal of American Chemical Society, vol. 52, pp. 633-635, (1930).
Muskopf et al., "Epoxy Resins", Ullmann's Encyclopedia of Industrial Chemistry, 5 Ed. vol. A9, pp. 547-562.
J.B. Conant et al., "Glycerol a,y-Dichlorophydrin," Organic Syntheses Coll., vol. 1, p. 292, 1941.
I. Miyakawa et al., Nagoya Sangyo Kagaku Kenkyusho Kenkyu Hokoku, 10, 49-52 (1957).
Han Xiu-Ying et al., Shanxi Daxue Xueba Bianjibu, 2002, 25(4), 379-80).
Jeffrey Lutje Spelberg, et al., A Tandem Enzyme Reaction to Produce Optically Active Halohydrins, Epoxides and Diols, Tetrahedron: Asymmetry, Elsevier Science Publishers, vol. 10, No. 15, pp. 2863-2870.
Oleoline, com, Glycerine Market report, $10^{th}$ Sep. 2003, No. 62.
Notification Under Act. No. 100/2001, Coll. As Amended by Act No. 93/2004, Coll. To the extent of Annex No. 4, (SPOLEK) Nov. 30, 2004.
Documentation Under Act No. 100/2001 Coll. As amended by Act No. 93/2004 Coll in the scope of appendix No. 4 (SPOLEK) Jan. 11, 2005.
Armando Novelli, "The Preparation of Moni- and Dichlorohydrins of Glycerol," Anal. Farm. Bioquim, vol. 1, 1930, pp. 8-19 (with English Abstract).
Derwent Publications, AN 109:6092 CA, JP 62-242638 (Oct. 23, 1987).
Derwent Publications, AN 1987-338139 [48], JP 62-242638, (Oct. 23, 1987).
Kirk-Othmer Encyclopedia of Chemical Technology, Third Edition, vol. 4, Blood, Coagulants and Anticoagulants to Cardiovascular Agents.
K. Weissermel and H J. Arpe in Industrial Organic Chemistry, Third, Completely Revised Edition, VCH, 1997, pp. 149,275.
Industrial Bioproducts: "Today and Tomorrow," Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & sons, Inc.
Ullmann's Encyclopedia of Industrial Chemistry, Fifth, Completely Revised Edition, 1985, vol. A13, pp. 292-293.
The Merck Index, Eleventh Edition, 1989, pp. 759-760.
Ullmann's Encyclopedia of Industrial Chemistry, Fifth Completely Revised Edition, vol. A1, pp. 427-429.
Ullmann's Encyclopedia of Industrial Chemistry, Fifth Completely REvised Edition, vol. A6, pp. 240-252.
Hancock, E.G., Propylene and its Industrial Derivatives, 1973, pp. 298-332.
K. Weissermel and H. J. Arpe in Industrial Organic Chemistry, Third, Completely Revised Edition, VCH 1997, pp. 149-163.
K. Weissermel and H. J. Arpe in Industrial Organic Chemistry, Third, Completely Revised Edition, VCH 1997, pp. 275-276.
Ullmann's Encyclopedia of Industrial Chemistry, Fifth Completely Revised Edition, vol. A9, pp. 539-540.
Perry's Chemical Engineers Handbook, Sixth Edition, Robert H. Perry, Don Green, 1984, Section 21-44 to 21-68.
Iwanami Dictionary of Physics and Chemistry, Third edition, Ryo Midorikawa/Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll,. as amended by later regulations of the project/intent combined process for the manufacture of epichlorohydrin (SPOLEK) Apr. 2005.
Berichte Der Deutschen Chemischen Gesellschaft, 1891, vol. 24, pp. 508-510.
Semendyava, N. D. et al., Khimicheskaya Promyshlennost, Seriya: Khornaya Promyshlennost (1981), 5, 21-2 (CA Summary) XP 002465275.
Rudnenko, E.V., et al., Kakokrasochnye Materialy I Ikh Primenenie (1988), 4, 69-71 (CA Summary) XP 002465276.
Kirk Othmer Encyclopedia of Chemical Technology, Third Edition, vol. 12, 1980, pp. 1002-1005.
Chemical Engineering Handbook, the $6^{th}$ Edition, Edited by the Chemical Engineers, published by Maruzen Co., Ltd., 1999, pp. 1296-1306 w/English translation of p. 1296, Table 28.4, p. 1298, left column, lines 4-13 and p. 1305, Table 28.10.
Herman A. Bruson, et al., "Thermal Decomposition of Glyceryl Carbonates," Journal of the American Chemical Society, vol. 74, Apr. 1952 pp. 2100-2101.
Product Brouchure of De Dietrich Company, Apr. 1996, pp. 3, 8 and 9 w/English translation of p. 8, left column, lines 1-4, p. 9.
The Journal of the American Chemical Society, vol. XLV, Jul.-Dec. 1923, pp. 2771-2772.
Perry's Chemical Engineers Handbook $7^{th}$ Ed. $11^{th}$ Section, 1997.
Perry's Chemical Engineers Handbook $7^{th}$ Ed. $13^{th}$ Section, 1997.
Perry's Chemical Engineers Handbook $7^{th}$ Ed. $15^{th}$ Section, 1997.
Ullmann Encyclopedia Industr. Chem. $5^{th}$ Ed., vol. A23, 1993, pp. 635-636.
Ullmann Encyclopedia Industr. Chem. $5^{th}$ Ed., vol. A13, 1989, pp. 289.
Ullmann Encyclopedia Industr. Chem. $5^{th}$ Ed., vol. All, 1988, pp. 354-360.
Catalogue of Nittetu Chemical Engineering Ltd. (Published in Mar. 1994).
12093 Chemicals, Chemical Daily Co., Ltd. (Published on Jan. 22, 1993) with attached English translation of relevant excerpts.
Chemicals Guide, Chemical Daily Co., Ltd. (Published on Jun. 15, 1990) with attached English translation of relevant excerpts.
Robert T. Morrison & Robert N. Boyd, Organic Chemistry, vol. II, pp. 666 to 667 and 712 to 714 (Japanese translation), published on Jul. 10, 1970, Tokyo Kagaku Dozin Co., Ltd. (and copies of similar passages but retrieved from the English $5^{th}$ Edition of the Book, 1987.
Klaus Weissermel, et al., "Industrial Organic Chemistry," ($3^{rd}$ Completely Revised Edition); VCH 1997. p. 347-355.
Myszkowski J. et al., "Removal of Chlorinated Organic Impurities from Hydrogen Chloride," CA, Jan. 1, 1900, XP002352444 (English CA Summary only).
Myszkowski J. et al., "Removal of Organic Compoiunds from Gaseous Hydrogen Chloride by an Absorption Method," CA, Jan. 1, 1900, XP002352445 (English CA summary only).
Milchert E. et al., "Recovering Hydrogen Chloride and Organic Chlor Compounds from the Reaction Mixture in the Chlorination of Ethylene," CA, Jan. 1, 1900, XP002352443 (English CA summary only).
Laine D.F., et al., "The Destruction of Organic Pollutants Under Mild Reaction Conditions ; A Review, " Microchemical Journal, vol. 85, No. 2, 2006, pp. 183-193.
Rainwater Harvesting and Utilization, Internet Citation, XP003003726.
H. Galeman, Organic Synthesis, Section 1, pp. 234-235.
Chemical Encyclopedia 5, p. 457.
Epoxy Resins, Shanghai Resin Plant, Shangai People's Press, 1971.
Martinetti Richard et al., "Environment Le Recyclage De l'eau," Industrie Textile, Ste. Sippe Sari, Metz, FR., No. 1300, Jul. 1, 1998, ISSN: 0019-9176.
Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).
Ying Ling Liu, "Phosphorous-Containing Epoxy Resins from a Novel Synthesis Route," Journal of Applied Polymer Science, vol. 83, 1697-1701 (2002).

E. Milchert et al., "Installation for the Recovery of Dichloropropanols and Epichlorohydrin from the Waste Water in Epichlorohydrin Production", Pol. J. Appl. Chem., vol. 41, p. 113-118 (1997).

Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- und Wassermengenwirtschaft e; V; - 2005 p. 81/-8/5., vol. 5.

Klaus Weissermel, et al., "Industrial Organic Chemistry," ($3^{rd}$ Completely Revised Edition); VCH 1997. p. 93-98.

Klaus Weissermel, et al., "Industrial Organic Chemistry," ($3^{rd}$ Completely Revised Edition); VCH 1997. p. 276-277.

M. Schellentrager, "Untersuchungen zur oxidation Entfarbung aus gewahlter Reaktivfarbstoffe: Analyse der Abbauprodukte miteels hochauflosender LC-MS", Diisertation, XP002548413 (Jan. 1, 2006) w/Attached English Abstract.

Medium and Long-Term Opportunities and Risks of the Biotechnologial Production of Bulk Chemicals from Renewable Resources—The Potential of White Biotechnology—The BREW Project—Final Report—Prepared under the European Commission's GRXTH Programme (DG Research) Utrecht, Sep. 2006 (pp. 29-31).

Ullmann Encyl. Industr. Chem., $5^{th}$ Ed., vol. A6, (1988), pp. 401-477.

Polymer Science Dictionary, M.S.M., Elsevier Applied Chemistry, London and New York 1989, p. 86.

Perry's chemical Engineers' Handbook, Sixth Edition, Section 21, pp. 21-55.

Ullmann's Encyclopedia of Industrial Chemistry, 2005, Wiley-VCH GmbH & Co., KgaA, Weinhem, pp. 8-15 and 401-477, Published online Mar. 15, 2001.

Ma Zengxin, Gan Yicui, Recovery of Polyglycerol from Residues of Synthetic Glycerol—Riyong Huaxue Gongye, 1997, 4, 21023 (Abstract Only).

Fauconnier, "Preparation of Epichlorohydrin," Bull. Soc. Chim. Fr., No. 122, pp. 212-214 (With English Translation).

RD 436093, Aug. 10, 2000, Research Disclosure.

Production and Prospect of the World Natural Glycerol by Zhu Shiyong, Cereals and Oils, vol. 1, 1997, pp. 33-38 (No English Translation).

Vinnolit; Vinnolit receives EU grant for water recycling project; Press Release, 2008: http://www.vinnolit.de/vinnolit.nsf/id/EN_Vinnolit_receives_EU_grant_for_water_recycling_project_.

N.W. Ziels, Journal of American Oil Chemists' Society, Nov. 1956, vol. 33, pp. 556-565.

Perry's Chemical Engineers Handbook, Sixth Edition, McGraw Hill Inc., (1984) Section 18.

Vol. B3: Unit Operations II of Ullmann's Encyclopedia of Industrial Chemistry, Fifth Completely Revised Edition, Published by VCH, 1988.

W. Giger et al., "14C/12C-Ratios in Organic Matter and Hydrocarbons Extracted from Dated Lake Sediments," Nuclear Instruments and Methods in Physics Research B5 (1984), 394-397. XP-002631954.

Jurgen O. Metzger, "Fats and Oils as Renewable Feedstock for Chemistry," Eur. J. Lipid Sci. Technol. (2009), 111, 865-876. XP-002631953.

Bruce M. Bell, "Glycerin as a Renewable Feedstock for Epichlorohydrin Production. The GTE Process," Clean-Soil, Air, Water, vol. 36, No. 8, (2008) pp. 657-661. XP-002631952.

Sang Hee Lee, et al., "Direct Preparation of Dichloropropanol (DCP) from Glycerol Using Heteropolyacid (HPA) Catalysts: A Catalyst Screen Study," Catalysis Communications (9), 2008, 1920-1923.

Azeotropic Data-III Compiled by Lee H. Horsley, The Dow Chemical Co., Midland, Mich., American Chemical Society (1973).

Yoshikazu Suzawa et al., Kagachu Sohchi (Chemical Apparatuses), vol. 23, No. 11, 3744, (published on Nov. 1981) with English translation.

Journal of American Oil Chemists' Society Jul. 1982, vol. 59, No. 7 pp. 292-295.

Chemical Engineering Handbook, 6th Revised Edition, 2nd print issued on Apr. 25, 2001, with attached English translation.

Organic synthesis, Part 1, published by Scientific Publishing, 1957.

Handbook of chemical products, organic chemical materials, Second edition, published by Chemical Industry Press, Jan. 1995.

R. A. Kiseleva and V.M. Goncharko, J. Appl. Chem. USSR, 1971, vol. 44, pp. 2086-2090.

Handbook of Corrosion data and material selection, published by Chemical Industry Press, edited by Jingyi Zuo, Yu Zuo; first edition, Oct. 1995 with attached English translation.

Handbook of azeotropic mixture, edited by information department of comprehensive scientific technology research institution of Fushun city, 1993.

Industry chemical reaction and application, pubished by Chinese Scientific Technology University Press, 1999 with attached English translation.

Epoxy resin, pubished by Shanghai People's Publishing House, 1971, with attached English translation.

Boschan and S. Winstein, Journal of the American Chemical Society, 1956, vol. 78, pp, 4921-4925.

Encyclopaedia for Chinese Adult Education, 1994, p. 623.

"Electrolytic cell test for electrolysis of epoxy sewage salt to prepare chlor-alkali", process Equipment Department of Research Institute of chlor-alkali, Shengyang chemical Plant, Liaononhg Chemical Industry, Issue No. 2, pp. 32-37, published Dec. 31, 1981, with attached English translation.

"Analysis of the Composition of the Byproduct During the Manufacturing Process of Sepichlorhydrin by GC-MS", Ren Chengxin et al., Chemical Analysis and Measurement, vol. 12, Issue No. 3, p. 25-26, Dec. 31, 2003, with attached English translation.

Encyclopedia of Chemical Technology, vol. 5, Nov. 1993.

Manufacture and use of epoxy resin, edited by Shanghai Resin Factory, published by China Petrochemical Press, First Edition, Oct. 1974.

METHOD FOR MAKING AN EPOXIDE

This application is a continuation application of U.S. application Ser. No. 11/914,879, filed Nov. 19, 2007, now allowed, incorporated herein by reference; which is a 371 of PCT/EP2006/062437, filed May 19, 2006; and claims the benefit of patent application FR 05 05120 and of patent application EP 05104321.4, both filed on 20 May 2005, and of provisional U.S. patent applications 60/734659, 60/734627, 60/734657, 60/734658, 60/734635, 60/734634, 60/734637 and 60/734636, all filed on 8 Nov. 2005, the content of which is incorporated here by reference.

The present invention relates to a process for preparing an epoxide. Epoxides are important raw materials for the production of other compounds.

Ethylene oxide is used, for example, for the production of ethylene glycol, of di- and polyethylene glycols, of mono-, di- and triethanolamines, etc. (see K. Weissermel and H.-J. Arpe in Industrial Organic Chemistry, Third, Completely Revised Edition, VCH, 1997, page 149). Propylene oxide is an important intermediate in the preparation of propylene 1,2-glycol, of dipropylene glycol, of ethers of propylene glycol, of isopropylamines, etc. (see K. Weissermel and H.-J. Arpe in Industrial Organic Chemistry, Third, Completely Revised Edition, VCH, 1997, page 275). Epichlorohydrin is an important raw material for the production of glycerol, of epoxy resins, of synthetic elastomers, of glycidyl ethers, of polyamide resins, etc. (see Ullmann's Encyclopedia of Industrial Chemistry, Fifth Edition, Vol. A9, p. 539).

In the industrial production of propylene oxide the most commonly used technology comprises the following steps: hypochloration of propylene to monochloropropanol and dehydrochloration of the monochloropropanol to propylene oxide by means of an aqueous alkaline solution.

In the industrial production of epichlorohydrin the most commonly used technology comprises the following steps: high-temperature free-radical substituted chlorination of propylene or allyl chloride, hypochlorination of the allyl chloride thus synthesized to dichloropropanol, and dehydrochlorination of the dichloropropanol to epichlorohydrin by means of an aqueous alkaline solution. Another technology, used on a smaller scale, comprises the following steps: catalytic acetoxylation of propylene to allyl acetate, hydrolysis of the allyl acetate to allyl alcohol, catalytic chlorination of the allyl alcohol to dichloropropanol, and alkaline dehydrochlorination of the dichloropropanol to epichlorohydrin. Other technologies, which have not yet gained industrial application, may be considered, including the direct catalytic oxidation of allyl chloride to epichlorohydrin using hydrogen peroxide, or the chlorination of glycerol to dichloropropanol, followed by alkaline dehydrochlorination of the dichloropropanol thus formed to epichlorohydrin.

In accordance with the invention it has been found that a problem, particularly when chlorohydrins are employed that are obtained by chlorinating polyhydroxylated aliphatic hydrocarbons in a dehydrochlorination reaction, is the presence of halogenated ketones formed as by-products. These halogenated ketones may have boiling temperatures close to those of the epoxides and may be difficult to separate by a distilling operation. In accordance with the invention it has also been found that the halogenated ketones, even at low concentration, are responsible for the development of an undesirable coloration of the epoxide or of products produced from it. This is more particularly the case for chloroacetone, which is formed in the process of dehydrochlorinating dichloropropanol to form epichlorohydrin.

It has also been found that, surprisingly, these ketones can be removed during the preparation of the epoxide.

The invention therefore provides a process for preparing an epoxide, wherein halogenated ketones are formed as by-products and which comprises at least one treatment to remove at least part of the halogenated ketones formed.

The invention provides more specifically a process for preparing an epoxide, wherein halogenated ketones are formed as by-products and which comprises at least one treatment intended to remove at least part of the halogenated ketones formed, and wherein the epoxide is prepared by dehydrochlorinating a chlorohydrin.

The chlorohydrin may be obtained by a process of hypochlorinating an olefin or by a process of chlorinating a polyhydroxylated aliphatic hydrocarbon, an ester of a polyhydroxylated aliphatic hydrocarbon or a mixture thereof.

The term "epoxide" is used here to describe a compound containing at least one oxygen bridged on a carbon-carbon bond. In general the carbon atoms of the carbon-carbon bond are adjacent and the compound may contain atoms other than carbon and oxygen atoms, such as hydrogen atoms and halogens. The preferred epoxides are ethylene oxide, propylene oxide, glycidol and epichlorohydrin.

The term "olefin" is used here to describe a compound containing at least one carbon-carbon double bond. In general the compound may contain atoms other than carbon atoms, such as hydrogen atoms and halogens. The preferred olefins are ethylene, propylene, allyl chloride and mixtures of at least two thereof.

The term "polyhydroxylated aliphatic hydrocarbon" refers to a hydrocarbon which contains at least two hydroxyl groups attached to two different saturated carbon atoms. The polyhydroxylated aliphatic hydrocarbon may contain, but is not limited to, from 2 to 60 carbon atoms.

Each of the carbons of a polyhydroxylated aliphatic hydrocarbon carrying the hydroxyl (OH) functional group may not possess more than one OH group and must be of sp3 hybridization. The carbon atom carrying the OH group may be primary, secondary or tertiary. The polyhydroxylated aliphatic hydrocarbon used in the present invention must contain at least two sp3-hybridized carbon atoms carrying an OH group. The polyhydroxylated aliphatic hydrocarbon includes any hydrocarbon containing a vicinal diol (1,2-diol) or a vicinal triol (1,2,3-triol), including higher orders of these repeating units, which are vicinal or contiguous. The definition of the polyhydroxylated aliphatic hydrocarbon also includes, for example, one or more 1,3-, 1,4-, 1,5- and 1,6-diol functional groups. The polyhydroxylated aliphatic hydrocarbon may also be a polymer such as polyvinyl alcohol. Geminal diols, for example, are excluded from this class of polyhydroxylated aliphatic hydrocarbons.

The polyhydroxylated aliphatic hydrocarbons may contain aromatic moieties or heteroatoms including, for example, heteroatoms of halogen, sulphur, phosphorus, nitrogen, oxygen, silicon and boron type, and mixtures thereof.

Polyhydroxylated aliphatic hydrocarbons which can be used in the present invention include, for example, 1,2-ethanediol(ethylene glycol), 1,2-propanediol(propylene glycol), 1,3-propanediol, 1-chloro-2,3-propanediol(chloropropanediol), 2-chloro-1,3-propanediol(chloropropanediol), 1,4-butanediol, 1,5-pentanediol, cyclohexanediols, 1,2-butanediol, 1,2-cyclohexanedimethanol, 1,2,3-propanetriol (also known as glycerol or glycerin), and mixtures thereof. With preference the polyhydroxylated aliphatic hydrocarbon used in the present invention includes, for example, 1,2-ethanediol, 1,2-propanediol, 1,3-propanediol, chloropropanediol and 1,2,3-propanetriol, and mixtures of at least two thereof. More preferably the polyhydroxylated aliphatic hydrocarbon used in the present invention includes, for example, 1,2-ethanediol, 1,2-propanediol, chloropropanediol and 1,2,3-propanetriol and mixtures of at least two thereof. 1,2,3-Propanetriol, or glycerol, is the most preferred.

The esters of polyhydroxylated aliphatic hydrocarbon may be present in the polyhydroxylated aliphatic hydrocarbon and/or may be produced in the process of preparing the chlorohydrin and/or may be prepared prior to the process of preparing the chlorohydrin. Examples of esters of polyhydroxylated aliphatic hydrocarbon include ethylene glycol monoacetate, propanediol monoacetates, glycerol monoacetates, glycerol monostearates, glycerol diacetates and mixtures thereof.

In the process according to the invention, the esters of the polyhydroxylated aliphatic hydrocarbon may originate from the reaction of the polyhydroxylated aliphatic hydrocarbon with an organic acid, before, during or within the steps which follow the reaction with the chlorinating agent.

The term "chlorohydrin" is used here to describe a compound containing at least one hydroxyl group and at least one chlorine atom which are attached to different saturated carbon atoms. A chlorohydrin which contains at least two hydroxyl groups is also a polyhydroxylated aliphatic hydrocarbon. Hence the starting material and the product of the reaction may each be chlorohydrins. In that case the "product" chlorohydrin is more chlorinated than the starting chlorohydrin; in other words, it has more chlorine atoms and fewer hydroxyl groups than the starting chlorohydrin. Preferred chlorohydrins are chloroethanol, chloropropanol, chloropropanediol, dichloropropanol and mixtures of at least two thereof. Dichloropropanol is particularly preferred. Chlorohydrins which are more particularly preferred are 2-chloroethanol, 1-chloropropan-2-ol, 2-chloropropan-1-ol, 1-chloropropane-2,3-diol, 2-chloropropane-1,3-diol, 1,3-dichloropropan-2-ol, 2,3-dichloropropan-1-ol and mixtures of at least two thereof.

The chlorohydrin in the process according to the invention may be obtained starting from fossil raw materials or starting from renewable raw materials, preferably starting from renewable raw materials.

By fossil raw materials are meant materials obtained from the treatment of petrochemical natural resources, for example petroleum, natural gas and coal. Among these materials the organic compounds containing 2 and 3 carbon atoms are preferred. When the chlorohydrin is dichloropropanol or chloropropanediol, allyl chloride, allyl alcohol and "synthetic" glycerol are particularly preferred. By "synthetic" glycerol is meant a glycerol obtained generally starting from petrochemical resources. When the chlorohydrin is chloroethanol, ethylene and "synthetic" ethylene glycol are particularly preferred. By "synthetic" ethylene glycol is meant an ethylene glycol obtained generally starting from petrochemical resources. When the chlorohydrin is monochloropropanol, propylene and "synthetic" propylene glycol are particularly preferred. By "synthetic" propylene glycol is meant a propylene glycol obtained generally starting from petrochemical resources.

By renewable raw materials are meant materials obtained from the treatment of renewable natural resources. Among these materials "natural" ethylene glycol, "natural" propylene glycol and "natural" glycerol are preferred. "Natural" ethylene glycol, propylene glycol and glycerol are obtained, for example, by conversion of sugars via thermochemical processes, it being possible for these sugars to be obtained starting from biomass, as described in "Industrial Bioproducts: Today and Tomorrow", Energetics, Incorporated for the U.S. Department of Energy, Office of Energy Efficiency and Renewable Energy, Office of the Biomass Program, July 2003, pages 49, 52 to 56. One of these processes is, for example, the catalytic hydrogenolysis of sorbitol obtained by thermochemical conversion of glucose. Another process is, for example, the catalytic hydrogenolysis of xylitol obtained by hydrogenating xylose. The xylose may be obtained, for example, by hydrolysing the hemicellulose present in maize fibres. By "natural glycerol" or by "glycerol obtained starting from renewable raw materials" is meant, in particular, glycerol obtained during the production of biodiesel or else glycerol obtained in the course of conversions of animal or vegetable oils or fats in general, such as saponification, transesterification or hydrolysis reactions.

Among the oils which can be used for preparing the natural glycerol mention may be made of all customary oils, such as palm oil, palm kernel oil, copra oil, babassu oil, former or new (low erucic acid) colza, sunflower oil, maize oil, castor oil and cotton oil, peanut oil, soyabean oil, linseed oil and crambe oil, and all oils obtained, for example, from sunflower or colza plants obtained by genetic modification or hybridization.

It is also possible to utilize used frying oils, various animal oils, such as fish oils, tallow, lard and even squaring greases.

Among the oils used it is also possible to indicate oils partially modified, for example, by polymerization or oligomerization, such as, for example, the stand oils of linseed oil and sunflower oil, and blown vegetable oils.

One particularly suitable glycerol may be obtained during the conversion of animal fats. Another particularly suitable glycerol may be obtained during the production of biodiesel. A third, very suitable glycerol may be obtained during the conversion of animal or vegetable oils or fats by transesterification in the presence of a heterogeneous catalyst, as described in documents FR 2752242, FR 2869612 and FR 2869613. More specifically, the heterogeneous catalyst is selected from mixed oxides of aluminium and zinc, mixed oxides of zinc and titanium, mixed oxides of zinc, titanium and aluminium, and mixed oxides of bismuth and aluminium, and the heterogeneous catalyst is employed in the form of a fixed bed. This latter process may be a biodiesel production process.

The chloroethanol may be obtained starting from these raw materials by any process. The processes of hypochlorinating ethylene and of chlorinating "synthetic" and/or "natural" ethylene glycol are preferred. The process of chlorinating "synthetic" and/or "natural" ethylene glycol is particularly preferred.

The chloropropanol may be obtained starting from these raw materials by any process. The processes of hypochlorinating propylene and chlorinating "synthetic" and/or "natural" propylene glycol are preferred. The process of chlorinating "synthetic" and/or "natural" propylene glycol is particularly preferred.

The chloropropanediol may be obtained starting from these raw materials by any process. The process of chlorinating "synthetic" and/or "natural" glycerol is preferred.

The dichloropropanol may be obtained starting from these raw materials by any process. The processes of hypochlorinating allyl chloride, chlorinating allyl alcohol and chlorinating "synthetic" and/or "natural" glycerol are preferred. The process of chlorinating "synthetic" and/or "natural" glycerol is particularly preferred.

In the process for preparing the epoxide according to the invention, it is preferable for at least a fraction of the chlorohydrin to be prepared by chlorinating a polyhydroxylated aliphatic hydrocarbon. The polyhydroxylated aliphatic hydrocarbon may be "synthetic" or "natural" in the senses defined above.

In the preparation process according to the invention, when the epoxide is epichlorohydrin, preference is given to "natural" glycerol, in other words glycerol obtained in the course of biodiesel production or in the course of conversions of animal or vegetable oils or fats, the conversions being selected from saponification, transesterification and hydrolysis reactions. Glycerol obtained by transesterification of fats or oils of vegetable or animal origin, the transesterification being carried out in the presence of a heterogeneous catalyst, is particularly preferred. In the process for preparing the epoxide according to the invention, the polyhydroxylated aliphatic hydrocarbon may be as described in the patent application "Process for preparing chlorohydrin by converting polyhydroxylated aliphatic hydrocarbons", filed in the name of SOLVAY SA on the same day as the present application, and the content of which is incorporated here by reference.

Particular mention is made of a process for preparing a chlorohydrin wherein a polyhydroxylated aliphatic hydrocarbon, an ester of a polyhydroxylated aliphatic hydrocarbon or a mixture thereof whose total metal content, the metals being expressed in the form of elements, is greater than or equal to 0.1 µg/kg and less than or equal to 1000 mg/kg, is reacted with a chlorinating agent.

A first advantage associated with this latter type of glycerol is that it contains little or no metals. These metals may be detrimental to certain steps in the preparation of dichloropropanol, such as, for example, residue treatment steps. A second advantage associated with this latter type of glycerol is that it contains little or no heavy organic compounds, which can accumulate in the preparation of dichloropropanol. The purge operations intended to remove these heavy organic products may consequently be reduced.

In the process for preparing the epoxide according to the invention, the chlorohydrin obtained starting from the polyhydroxylated aliphatic hydrocarbon by reaction with a chlorinating agent may be employed, for example, in accordance with the process described in application WO 2005/054167 of SOLVAY SA, the content of which is incorporated here by reference.

In the process for preparing the epoxide according to the invention, the polyhydroxylated aliphatic hydrocarbon may be a crude product or a purified product as described in application WO 2005/054167 of SOLVAY SA, from page 2 line 8 to page 4 line 2.

The crude product may contain fatty acids, fatty acid esters such as, in particular, monoglycerides and diglycerides, optionally in combination with water or a metal salt. Preference is given to using a purified glycerol, i.e. one containing at least 80% and not more than 99.9% by weight of glycerol, at least 0.1% and not more than 20% by weight of water, at least 1 mg/kg and not more than 0.1% by weight of aldehyde, and at least 10 mg/kg and not more than 10% by weight of methanol and/or ethanol.

In the process for preparing the epoxide according to the invention, the polyhydroxylated aliphatic hydrocarbon may be a polyhydroxylated aliphatic hydrocarbon whose alkali metal and/or alkaline earth metal content is less than or equal to 5 g/kg, as described in the application entitled "Process for preparing a chlorohydrin by chlorinating a polyhydroxylated aliphatic hydrocarbon", filed in the name of SOLVAY SA on the same day as the present application, and the content of which is incorporated here by reference.

In the process according to the invention, the alkali metal and/or alkaline earth metal content of the polyhydroxylated aliphatic hydrocarbon, the ester of a polyhydroxylated aliphatic hydrocarbon or a mixture thereof is less than or equal to 5 g/kg, often less than or equal to 1 g/kg, more particularly less than or equal to 0.01 g/kg and, in certain cases, less than or equal to 2 mg/kg. The alkali metal and/or alkaline earth metal content of the polyhydroxylated aliphatic hydrocarbon is generally greater than or equal to 0.1 µg/kg.

In the process according to the invention, the alkali metals are generally lithium, sodium, potassium and caesium, often sodium and potassium, and frequently sodium.

In the process for preparing a chlorohydrin according to the invention, the lithium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. Said content is generally greater than or equal to 0.1 µg/kg.

In the process according to the invention, the sodium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. Said content is generally greater than or equal to 0.1 µg/kg.

In the process according to the invention, the potassium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. Said content is generally greater than or equal to 0.1 µg/kg.

In the process according to the invention, the rubidium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. Said content is generally greater than or equal to 0.1 µg/kg.

In the process according to the invention, the caesium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. Said content is generally greater than or equal to 0.1 µg/kg.

In the process according to the invention, the alkaline earth elements are generally magnesium, calcium, strontium and barium, often magnesium and calcium, and frequently calcium.

In the process according to the invention, the magnesium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. Said content is generally greater than or equal to 0.1 µg/kg.

In the process according to the invention, the calcium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. Said content is generally greater than or equal to 0.1 mg/kg.

In the process according to the invention, the strontium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. Said content is generally greater than or equal to 0.1 µg/kg.

In the process according to the invention, the barium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. Said content is generally greater than or equal to 0.1 µg/kg.

In the process according to the invention, the alkali metals and/or alkaline earth metals are generally present in the form of salts, frequently in the form of chlorides, sulphates and mixtures thereof. Sodium chloride is the most often encountered.

In the process for preparing the epoxide according to the invention, the chlorinating agent of the polyhydroxylated aliphatic hydrocarbon may be hydrogen chloride and/or hydrochloric acid as described in application WO 2005/054167 of SOLVAY SA, from page 4 line 30 to page 6 line 2.

The hydrogen chloride may originate from a process for pyrolysing organic chlorine compounds, such as, for example, a vinyl chloride preparation, a process for preparing 4,4-methylenediphenyl diisocyanate (MDI) or toluene diisocyanate (TDI), metal pickling processes, or the reaction of an inorganic acid such as sulphuric or phosphoric acid with a metal chloride such as sodium chloride, potassium chloride or calcium chloride.

In one advantageous embodiment of the process for preparing the epoxide according to the invention, the chlorinating agent of the polyhydroxylated aliphatic hydrocarbon is gaseous hydrogen chloride or an aqueous solution of hydrogen chloride or a combination of the two.

In the process for preparing the epoxide according to the invention, the chlorinating agent of the polyhydroxylated aliphatic hydrocarbon may be aqueous hydrochloric acid or hydrogen chloride, preferably anhydrous, obtained from a process for preparing allyl chloride and/or chloromethanes and/or of chlorinolysis and/or of high-temperature oxidation of chlorine compounds, as described in the application entitled "Process for preparing a chlorohydrin by reacting a polyhydroxylated aliphatic hydrocarbon with a chlorinating agent", filed in the name of SOLVAY SA on the same day as the present application, and the content of which is incorporated here by reference.

Particular mention is made of a process for preparing a chlorohydrin from a polyhydroxylated aliphatic hydrocarbon, an ester of a polyhydroxylated aliphatic hydrocarbon or a mixture thereof and a chlorinating agent, the latter agent containing at least one of the following compounds: nitrogen, oxygen, hydrogen, chlorine, an organic hydrocarbon compound, an organic halogen compound, an organic oxygen compound and a metal.

Particular mention is made of an organic hydrocarbon compound selected from saturated or unsaturated aliphatic and aromatic hydrocarbons and mixtures thereof.

Particular mention is made of an unsaturated aliphatic hydrocarbon selected from acetylene, ethylene, propylene, butene, propadiene, methylacetylene and mixtures thereof, of a saturated aliphatic hydrocarbon selected from methane, ethane, propane, butane and mixtures thereof, and of an aromatic hydrocarbon which is benzene.

Particular mention is made of an organic halogen compound which is an organic chlorine compound selected from chloromethanes, chloroethanes, chloropropanes, chlorobutanes, vinyl chloride, vinylidene chloride, monochloropropenes, perchloroethylene, trichloroethylene, chlorobutadienes, chlorobenzenes and mixtures thereof.

Particular mention is made of an organic halogen compound which is an organic fluorine compound selected from fluoromethanes, fluoroethanes, vinyl fluoride, vinylidene fluoride and mixtures thereof.

Particular mention is made of an organic oxygen compound selected from alcohols, chloroalcohols, chloroethers and mixtures thereof.

Particular mention is made of a metal selected from alkali metals, alkaline earth metals, iron, nickel, copper, lead, arsenic, cobalt, titanium, cadmium, antimony, mercury, zinc, selenium, aluminium, bismuth and mixtures thereof.

Mention is made more particularly of a process wherein the chlorinating agent is obtained at least partly from a process for preparing allyl chloride and/or from a process for preparing chloromethanes and/or from a process of chlorinolysis and/or from a process of oxidizing chlorine compounds at a temperature greater than or equal to 800° C.

In one advantageous embodiment of the process for preparing the epoxide according to the invention, the chlorinating agent of the polyhydroxylated aliphatic hydrocarbon contains no gaseous hydrogen chloride.

In the process for preparing the epoxide according to the invention, the reaction of chlorinating the polyhydroxylated aliphatic hydrocarbon may be carried out in a reactor as described in application WO 2005/054167 of SOLVAY SA, at page 6 lines 3 to 23.

Mention is made particularly of plant made of or covered with materials which under the reaction conditions are resistant to chlorinating agents, especially to hydrogen chloride. Mention is made more particularly of plant made of enamelled steel or of tantalum.

In the process for preparing the epoxide according to the invention, the reaction of chlorinating the polyhydroxylated aliphatic hydrocarbon, the ester of polyhydroxylated aliphatic hydrocarbon or the mixture thereof may be carried out in apparatus made of or covered with materials which are resistant to chlorinating agents, as described in the application entitled "Process for preparing a chlorohydrin in corrosion-resistant apparatus", filed in the name of SOLVAY SA on the same day as the present application, and the content of which is incorporated here by reference.

Particular mention is made of a process for preparing a chlorohydrin which comprises a step wherein a polyhydroxylated aliphatic hydrocarbon, an ester of polyhydroxylated aliphatic hydrocarbon or a mixture thereof is subjected to reaction with a chlorinating agent containing hydrogen chloride and at least one other step carried out in apparatus made of or covered with materials resistant to the chlorinating agent under the conditions in which said step is performed. Mention is made more particularly of metallic materials such as enamelled steel, gold and tantalum and of non-metallic materials such as high-density polyethylene, polypropylene, poly(vinylidene fluoride), polytetrafluoroethylene, perfluoroalkoxyalkanes and poly(perfluoropropyl vinyl ether), polysulphones and polysulphides, and graphite, including impregnated graphite.

In the process for preparing the epoxide according to the invention, the reaction of chlorinating the polyhydroxylated aliphatic hydrocarbon, the ester of polyhydroxylated aliphatic hydrocarbon or the mixture thereof may be carried out in a reaction mixture as described in the application entitled "Continuous process for preparing chlorohydrins", filed in the name of SOLVAY SA on the same day as the present application, and the content of which is incorporated here by reference.

Particular mention is made of a continuous process for producing chlorohydrin wherein a polyhydroxylated aliphatic hydrocarbon, an ester of a polyhydroxylated aliphatic hydrocarbon or a mixture thereof is reacted with a chlorinating agent and an organic acid in a liquid reaction mixture whose steady-state composition comprises polyhydroxylated aliphatic hydrocarbon and esters of polyhydroxylated aliphatic hydrocarbon with a sum content, expressed in moles of polyhydroxylated aliphatic hydrocarbon, of more than 1.1 mol % and less than or equal to 30 mol %, the percentage being based on the organic part of the liquid reaction mixture.

The organic part of the liquid reaction mixture consists of all of the organic compounds in the liquid reaction mixture, in other words the compounds whose molecule contains at least 1 carbon atom.

In the process for preparing the epoxide according to the invention, the reaction of chlorinating the polyhydroxylated aliphatic hydrocarbon may be carried out in the presence of a catalyst as described in application WO 2005/054167 of SOLVAY SA, from page 6 line 28 to page 8 line 5.

Mention is made particularly of a catalyst based on a carboxylic acid or on a carboxylic acid derivative having an atmospheric boiling point of greater than or equal to 200° C., especially adipic acid and adipic acid derivatives.

In the process for preparing the epoxide according to the invention, the reaction of chlorinating the polyhydroxylated aliphatic hydrocarbon may be carried out at a catalyst concentration, temperature and pressure and for residence times as described in application WO 2005/054167 of SOLVAY SA, from page 8 line 6 to page 10 line 10.

Mention is made particularly of a temperature of at least 20° C. and not more than 160° C., a pressure of at least 0.3 bar and not more than 100 bar and a residence time of at least 1 h and not more than 50 h.

In the process for preparing the epoxide according to the invention, the reaction of chlorinating the polyhydroxylated aliphatic hydrocarbon may be carried out in the presence of a solvent as described in application WO 2005/054167 of SOLVAY SA, at page 11 lines 12 to 36.

Mention is made particularly of an organic solvent such as chlorinated organic solvent, an alcohol, a ketone, an ester or an ether, a non-aqueous solvent which is miscible with the polyhydroxylated aliphatic hydrocarbon, such as chloroethanol, chloropropanol, chloropropanediol, dichloropropanol, dioxane, phenol, cresol, and mixtures of chloropropanediol and dichloropropanol, or heavy reaction products such as at least partly chlorinated and/or esterified oligomers of the polyhydroxylated aliphatic hydrocarbon.

In the process for preparing the epoxide according to the invention, the reaction of chlorinating the polyhydroxylated aliphatic hydrocarbon may be carried out in the presence of a liquid phase comprising heavy compounds other than the polyhydroxylated aliphatic hydrocarbon, as described in the application entitled "Process for preparing a chlorohydrin in a liquid phase", filed in the name of SOLVAY SA on the same day as the present application, and the content of which is incorporated here by reference.

Particular mention is made of a process for preparing a chlorohydrin wherein a polyhydroxylated aliphatic hydrocarbon, an ester of polyhydroxylated aliphatic hydrocarbon or a mixture thereof is subjected to reaction with a chlorinating agent in the presence of a liquid phase comprising heavy compounds other than the polyhydroxylated aliphatic hydrocarbon, the boiling temperature of said compounds under a pressure of 1 bar absolute being at least 15° C. greater than the boiling temperature of the chlorohydrin under a pressure of 1 bar absolute.

In the process for preparing the epoxide according to the invention, the reaction of chlorinating the polyhydroxylated aliphatic hydrocarbon, the ester of polyhydroxylated aliphatic hydrocarbon or the mixture thereof may be carried out in batch mode or in continuous mode. Continuous mode is particularly preferred.

In the process of preparing the epoxide according to the invention, the reaction of chlorinating the polyhydroxylated aliphatic hydrocarbon is preferably carried out in a liquid reaction mixture. The liquid reaction mixture may be single-phase or multi-phase.

The liquid reaction mixture is composed of the entirety of the dissolved or dispersed solid compounds, dissolved or dispersed liquid compounds and dissolved or dispersed gaseous compounds at the reaction temperature.

The reaction mixture comprises the reactants, the catalyst, the solvent, the impurities present in the reactants, in the solvent and in the catalyst, the reaction intermediates, the reaction products and the reaction by-products.

By reactants are meant the polyhydroxylated aliphatic hydrocarbon, the ester of polyhydroxylated aliphatic hydrocarbon and the chlorinating agent.

The impurities present in the polyhydroxylated aliphatic hydrocarbon may include carboxylic acids, salts of carboxylic acids, fatty acid esters with the polyhydroxylated aliphatic hydrocarbon, fatty acid esters with the alcohols used in the transesterification, and inorganic salts such as alkali metal or alkaline earth metal sulphates and chlorides.

When the polyhydroxylated aliphatic hydrocarbon is glycerol, the impurities of the glycerol may include carboxylic acids, salts of carboxylic acids, fatty acid esters such as mono-, di- and triglycerides, fatty acid esters with the alcohols used in the transesterification, and inorganic salts such as alkali metal or alkaline earth metal sulphates and chlorides.

The reaction intermediates may include monochlorohydrins of the polyhydroxylated aliphatic hydrocarbon and their esters and/or polyesters, the esters and/or polyesters of the polyhydroxylated aliphatic hydrocarbon, and the esters of polychlorohydrins.

When the chlorohydrin is dichloropropanol, the reaction intermediates may include the monochlorohydrin of glycerol and its esters and/or polyesters, the esters and/or polyesters of glycerol, and the esters of dichloropropanol.

The ester of polyhydroxylated aliphatic hydrocarbon may therefore be, as appropriate, a reactant, an impurity of the polyhydroxylated aliphatic hydrocarbon or a reaction intermediate.

By reaction products are meant the chlorohydrin and water. The water may be the water formed in the chlorination reaction and/or may be the water introduced into the process, for example via the polyhydroxylated aliphatic hydrocarbon and/or the chlorinating agent, as described in application WO 2005/054167 of SOLVAY SA, at page 2 lines 22 to 28, at page 3 lines 20 to 25, at page 5 lines 7 to 31 and at page 12 lines 14 to 19.

The by-products may include, for example, partly chlorinated and/or esterified oligomers of the polyhydroxylated aliphatic hydrocarbon.

When the polyhydroxylated aliphatic hydrocarbon is glycerol, the by-products may include, for example, the partly chlorinated and/or esterified oligomers of glycerol.

The reaction intermediates and the by-products may be formed in the various steps of the process, such as, for example, during the step of preparing the chlorohydrin and during the steps of separating off the chlorohydrin.

The liquid reaction mixture may thus comprise the polyhydroxylated aliphatic hydrocarbon, the chlorinating agent, dissolved or dispersed in the form of bubbles, the catalyst, the solvent, the impurities present in the reactants, the solvent and the catalyst, such as dissolved or solid salts, for example, the reaction intermediates, the reaction products and the reaction by-products.

In the process according to the invention, the chlorohydrin may be separated from the other compounds of the reaction mixture in accordance with methods as described in application WO 2005/054167 of SOLVAY SA, from page 12 line 1 to page 16 line 35 and at page 18 lines 6 to 13. Particular mention is made of separation by azeotropic distillation of a water/chlorohydrin/chlorinating agent mixture under conditions which minimize the losses of chlorinating agent, followed by separation of the chlorohydrin by decantation. These other compounds are those mentioned above, and include unconsumed reactants, the impurities present in the reactants, the catalyst and the solvent, the solvent, the catalyst, the reaction intermediates, the water and the reaction by-products.

In the process for preparing the epoxide according to the invention, the separation of the chlorohydrin and the other compounds from the reaction mixture from chlorination of the polyhydroxylated aliphatic hydrocarbon may be carried out according to methods as described in patent application EP 05104321.4, filed in the name of SOLVAY SA on 20 May 2005, and the content of which is incorporated here by reference.

Particular mention is made of a process for preparing a chlorohydrin by reacting a polyhydroxylated aliphatic hydrocarbon, an ester of a polyhydroxylated aliphatic hydrocarbon or a mixture thereof with a chlorinating agent wherein the polyhydroxylated aliphatic hydrocarbon, an ester of a polyhydroxylated aliphatic hydrocarbon or a mixture thereof that is used contains at least one solid or dissolved metal salt, the process including a separating operation intended to remove part of the metal salt. Mention is made more particularly of a process for preparing a chlorohydrin by reacting a polyhydroxylated aliphatic hydrocarbon, an ester of a polyhydroxylated aliphatic hydrocarbon of a mixture thereof with a chlorinating agent wherein the polyhydroxylated aliphatic hydrocarbon, an ester of a polyhydroxylated aliphatic hydrocarbon or a mixture thereof that is used contains at least one sodium and/or potassium chloride and/or sulphate and wherein the separating operation intended to remove part of the metal salt is a filtering operation. Mention is also made particularly of a process for preparing a chlorohydrin wherein (a) a polyhydroxylated aliphatic hydrocarbon, an ester of a polyhydroxylated aliphatic hydrocarbon or a mixture thereof is subjected to reaction with a chlorinating agent in a reaction mixture, (b) a fraction of the reaction mixture containing at least the water and the chlorohydrin is removed continuously or periodically, (c) at least one part of the fraction obtained in step (b) is introduced into a distillation step, and (d) the reflux ratio of the distillation step is controlled by supplying water to said distillation step. Mention is made very particularly of a process for preparing a chlorohydrin wherein (a) a polyhydroxylated aliphatic hydrocarbon, an ester of a polyhydroxylated aliphatic hydrocarbon or a mixture thereof is subjected to reaction with hydrogen chloride in a reaction mixture, (b) a fraction of the reaction mixture containing at least the water in the chlorohydrin is removed continuously or periodically, (c) at least part of the fraction obtained in step (b) is introduced into a distillation step, wherein the ratio between the hydrogen chloride concentration and the water concentration in the fraction introduced into the distillation step is smaller than the ratio of hydrogen chloride/water concentrations in the binary azeotropic hydrogen chloride/water composition at the distillation temperature and pressure.

In the process for preparing the epoxide according to the invention, the chlorohydrin and the other compounds can be separated from the reaction mixture from chlorination of the polyhydroxylated aliphatic hydrocarbon, ester of polyhydroxylated aliphatic hydrocarbon or mixtures thereof by methods as described in the application entitled "Process for preparing a chlorohydrin", filed in the name of SOLVAY SA on the same day as the present application, and the content of which is incorporated here by reference.

Particular mention is made of a process for preparing a chlorohydrin comprising the following steps: (a) a polyhydroxylated aliphatic hydrocarbon, an ester of a polyhydroxylated aliphatic hydrocarbon or a mixture thereof is reacted with a chlorinating agent and an organic acid so as to give a mixture containing the chlorohydrin and esters of a chlorohydrin, (b) at least part of the mixture obtained in step (a) is subjected to one or more treatments in steps subsequent to step (a), and (c) polyhydroxylated aliphatic hydrocarbon is added to at least one of the steps subsequent to step (a), so as to react, at a temperature greater than or equal to 20° C., with the esters of the chlorohydrin, so as to form, at least partly, esters of the polyhydroxylated aliphatic hydrocarbon.

Mention is made more particularly of a process wherein the polyhydroxylated aliphatic hydrocarbon is glycerol and the chlorohydrin is dichloropropanol.

In the process for preparing the epoxide according to the invention, the chlorohydrin and the other compounds can be separated from the reaction mixture from chlorination of the polyhydroxylated aliphatic hydrocarbon, ester of polyhydroxylated aliphatic hydrocarbon or a mixture thereof by methods as described in the application entitled "Process for preparing a chlorohydrin starting from a polyhydroxylated aliphatic hydrocarbon", filed in the name of SOLVAY SA on the same day as the present application, and the content of which is incorporated here by reference.

Particular mention is made of a process for preparing chlorohydrin by reacting a polyhydroxylated aliphatic hydrocarbon, an ester of polyhydroxylated hydrocarbon or a mixture thereof with a chlorinating agent in a reactor which is supplied with one or more liquid streams containing less than 50% by weight of the polyhydroxylated aliphatic hydrocarbon, the ester of polyhydroxylated hydrocarbon or the mixture thereof, relative to the weight of the entirety of the liquid streams introduced into the reactor. More particular mention is made of a process comprising the following steps: (a) a polyhydroxylated aliphatic hydrocarbon, an ester of polyhydroxylated hydrocarbon or a mixture thereof is reacted with a chlorinating agent so as to give at least one mixture containing the chlorohydrin, water and the chlorinating agent, (b) at least a fraction of the mixture formed in step (a) is removed, and (c) the fraction removed in step (b) is subjected to a distilling and/or stripping operation wherein polyhydroxylated aliphatic hydrocarbon is added in order to separate, from the fraction removed in step (b), a mixture containing water and the chlorohydrin, having a reduced chlorinating agent content as compared with that of the fraction removed in step (b).

In the process for preparing the epoxide according to the invention, the chlorohydrin and the other compounds of the reaction mixture from chlorination of the polyhydroxylated aliphatic hydrocarbon may be separated by methods as described in the application entitled "Process for converting polyhydroxylated aliphatic hydrocarbons into chlorohydrins", filed in the name of SOLVAY SA on the same day as the present application, and the content of which is incorporated here by reference.

Particular mention is made of a process for preparing a chlorohydrin comprising the following steps: (a) a polyhydroxylated aliphatic hydrocarbon, an ester of a polyhydroxylated aliphatic hydrocarbon or a mixture thereof is reacted with a chlorinating agent so as to give a mixture containing the chlorohydrin, chlorohydrin esters and water, (b) at least a fraction of the mixture obtained in step (a) is subjected to a distilling and/or stripping treatment so as to give a batch concentrated with water, with chlorohydrin and with chlorohydrin esters, and (c) at least a fraction of the batch obtained in step (b) is subjected to a separating operation in the presence of at least one additive so as to give a portion concentrated with chlorohydrin and with chlorohydrin esters and containing less than 40% by weight of water.

The separating operation is more particularly a decantation.

In the process for preparing the epoxide according to the invention, the separation and the treatment of the other compounds of the reaction mixture from chlorination of the polyhydroxylated aliphatic hydrocarbon may be carried out by methods as described in the application entitled "Process for preparing a chlorohydrin by chlorinating a polyhydroxylated aliphatic hydrocarbon", filed in the name of SOLVAY SA on the same day as the present application. One preferred treatment consists in subjecting a fraction of the reaction by-products to a high-temperature oxidation.

Particular mention is made of a process for preparing a chlorohydrin comprising the following steps: (a) a polyhydroxylated aliphatic hydrocarbon, an ester of a polyhydroxylated aliphatic hydrocarbon or a mixture thereof whose alkali metal and/or alkaline earth metal content is less than or equal to 5 g/kg, an chlorinating agent and an organic acid are reacted so as to give a mixture containing at least the chlorohydrin and by-products, (b) at least part of the mixture obtained in step (a) is subjected to one or more treatments in steps subsequent to step (a), and (c) at least one of the steps subsequent to step (a) consists in an oxidation at a temperature greater than or equal to 800° C.

More particular mention is made of a process wherein, in the subsequent step, a part of the mixture obtained in step (a) is removed and this part is subjected to oxidation at a temperature greater than or equal to 800° C. in the course of its removal. Particular mention is also made of a process wherein the treatment of step (b) is a separating operation selected from phase separation, filtration, centrifugation, extraction, washing, evaporation, stripping, distillation and adsorption operations or combinations of at least two thereof.

In the process according to the invention, when the chorohydrin is chloropropanol, said chloropropanol is generally obtained in the form of a mixture of compounds comprising the isomers of 1-chloropropan-2-ol and of 2-chloropropan-1-ol. This mixture generally contains more than 1% by weight of the two isomers, preferably more than 5% by weight and in particular more than 50%. The mixture usually contains less than 99.9% by weight of the two isomers, preferably less than 95% by weight and very particularly less than 90% by weight. The other constituents of the mixture may be compounds originating from the processes for preparing the chloropropanol, such as residual reactants, reaction by-products, solvents and, in particular, water.

The mass ratio between the isomers 1-chloropropan-2-ol and 2-chloropropan-1-ol is usually greater than or equal to 0.01, preferably greater than or equal to 0.4. This ratio is usually less than or equal to 99 and preferably less than or equal to 25.

In the process according to the invention, when the chorohydrin is chloroethanol, said chloroethanol is generally obtained in the form of a mixture of compounds comprising the isomer 2-chloroethanol. This mixture generally contains more than 1% by weight of the isomer, preferably more than 5% by weight and in particular more than 50%. The mixture usually contains less than 99.9% by weight of the isomer, preferably less than 95% by weight and very particularly less than 90% by weight. The other constituents of the mixture may be compounds originating from the processes for preparing the chloroethanol, such as residual reactants, reaction by-products, solvents and, in particular, water.

In the process according to the invention, when the chlorohydrin is dichloropropanol, said dichloropropanol is generally obtained in the form of a mixture of compounds comprising the isomers of 1,3-dichloropropan-2-ol and of 2,3-dichloropropan-1-ol. This mixture generally contains more than 1% by weight of the two isomers, preferably more than 5% by weight and in particular more than 50%. The mixture usually contains less than 99.9% by weight of the two isomers, preferably less than 95% by weight and very particularly less than 90% by weight. The other constituents of the mixture may be compounds originating from the processes for preparing the dichloropropanol, such as residual reactants, reaction by-products, solvents and, in particular, water.

The mass ratio between the isomers 1,3-dichloropropan-2-ol and 2,3-dichloropropan-1-ol is usually greater than or equal to 0.01, preferably greater than or equal to 0.4. This ratio is usually less than or equal to 99 and preferably less than or equal to 25.

In the process according to the invention, when the chlorohydrin is dichloropropanol and is obtained in a process starting from allyl chloride, the isomer mixture exhibits a 1,3-dichloropropan-2-ol:2,3-dichloropropan-1-ol mass ratio which is often from 0.3 to 0.6, typically approximately 0.5. When the dichloropropanol is obtained in a process starting from synthetic and/or natural glycerol, the 1,3-dichloropropan-2-ol:2,3-dichloropropan-1-ol mass ratio is commonly greater than or equal to 1.5, often greater than or equal to 3.0, frequently greater than or equal to 7.0 and very particularly greater than or equal to 20.0. When the dichloropropanol is obtained starting from allyl alcohol, the 1,3-dichloropropan-2-ol:2,3-dichloropropan-1-ol mass ratio is often of the order of 0.1.

By halogenated ketones are meant ketones containing 3 to 18 carbon atoms, preferably 3 to 12 carbon atoms and, with particular preference, 3 to 6 carbon atoms, and in which one or more hydrogen atoms have been replaced by a halogen atom. They are often chlorinated ketones, and more particularly chloroacetone.

These halogenated ketones may be produced under certain conditions during and/or prior to the dehydrochlorination of the chlorohydrin in the processes for preparing the chlorohydrin. In the first case, when the chlorohydrin is dichloropropanol, and without wishing to be tied by any one theory, it is thought that the chloroacetone is essentially generated starting from the isomer 1,3-dichloropropan-2-ol. In the second case, it has been found, surprisingly, that the halogenated ketones may be present in a large amount in the chlorohydrin obtained by a process of hydrochlorinating a polyhydroxylated aliphatic hydrocarbon. In this case the halogenated ketone content of the chlorohydrin obtained is commonly greater than or equal to 0.005% by weight, relative to the mixture of the isomers of the chlorohydrin, and often greater than or equal to 0.01% by weight. Said content is commonly less than or equal to 0.4% by weight, relative to the mixture of isomers of the chlorohydrin, and preferably less than or equal to 0.3% by weight.

According to a first variant of the process according to the invention, the treatment intended to remove at least part of the halogenated ketones is carried out during the dehydrochlorination of the chlorohydrin.

By dehydrochlorination is meant the removal of hydrochloric acid, irrespective of the mechanism of this removal and the ultimate form in which the hydrochloric acid removed is obtained.

The dehydrochlorination may be carried out by any known means, for example by heating the chlorohydrin in the absence of any reactant other than the chlorohydrin, by treating the chlorohydrin with a basic compound, in the presence or absence of a catalyst. It is preferred to carry out the dehydrochlorination by treating the chlorohydrin with a basic compound.

By basic compound is meant basic organic compounds or basic inorganic compounds. Basic inorganic compounds are preferred. These basic inorganic compounds may be oxides, hydroxides and salts of metals, such as carbonates, hydrogen carbonates, phosphates or mixtures thereof, for example. Among the metals, preference is given to alkali metals and alkaline earth metals. Sodium, potassium and calcium and mixtures thereof are particularly preferred. The basic inorganic compounds may be present in the form of solids, liquids or aqueous or organic solutions or suspensions. Aqueous solutions or suspensions are preferred. The solutions and suspensions of NaOH, of $Ca(OH)_2$, purified alkaline brine and mixtures thereof are particularly preferred. By purified alkaline brine is meant the caustic soda, containing NaCl, of the kind produced in a diaphragm electrolysis process. The amount of basic compound in the solution or suspension is generally greater than or equal to 1% by weight, preferably greater than or equal to 4% by weight and with very particular preference greater than or equal to 6% by weight. This amount is commonly less than or equal to 60% by weight. An amount of approximately 50% by weight is particularly appropriate.

The basic compound may be used in superstoichiometric, substoichiometric or stoichiometric amounts with respect to the chlorohydrin. When the basic compound is used in substoichiometric amounts it is usual to use not more than 2 moles of chlorohydrin per mole of base. It is common to use not more than 1.5 moles of chlorohydrin per mole of base and preferably not more than 1.05 moles of chlorohydrin per mole of base. When the basic agent is used in superstoichiometric amounts use is made of not more than 2 moles of base per mole of chlorohydrin. In this case it is customary to use at least 1.05 moles of base per mole of chlorohydrin.

The water content of the mixture comprising the chlorohydrin and the basic compound is generally greater than or equal to 8% by weight.

When the dehydrochlorination is carried out by treating the chlorohydrin with a basic compound, the reaction mixture may also contain a solvent such as those described in patent U.S. Pat. No. 3,061,615 in the name of SOLVAY SA.

The dehydrochlorination may be carried out as described in the application entitled "Process for preparing an epoxide starting from a polyhydroxylated aliphatic hydrocarbon and a chlorinating agent", filed in the name of SOLVAY SA on the same day as the present application, and the content of which is incorporated here by reference.

Particular mention is made of a process for preparing an epoxide wherein a reaction mixture resulting from the reaction of a polyhydroxylated aliphatic hydrocarbon, an ester of a polyhydroxylated aliphatic hydrocarbon or a mixture thereof with a chlorinating agent, the reaction mixture containing at least 10 g of chlorohydrin per kg of reaction mixture, is subjected to a subsequent chemical reaction without treatment in between.

Mention is also made of the preparation of an epoxide comprising the following steps: (a) a polyhydroxylated aliphatic hydrocarbon, an ester of a polyhydroxylated aliphatic hydrocarbon or a mixture thereof is reacted with a chlorinating agent and an organic acid so as to form the chlorohydrin and chlorohydrin esters in a reaction mixture containing the polyhydroxylated aliphatic hydrocarbon, the ester of polyhydroxylated aliphatic hydrocarbon, water, the chlorinating agent and the organic acid, the reaction mixture containing at least 10 g of chlorohydrin per kg of reaction mixture, (b) at least a fraction of the reaction mixture obtained in step (a), said fraction having the same composition as the reaction mixture obtained in step (a), is subjected to one or more treatments in steps subsequent to step (a), and (c) a basic compound is added to at least one of the steps subsequent to step (a) so as to react at least partly with the chlorohydrin, the chlorohydrin esters, the chlorinating agent and the organic acid so as to form the epoxide and salts.

The liquid reaction mixture may be single-phase or biphase.

The basic dehydrochlorination treatment may be executed in continuous or discontinuous mode.

The duration of the basic treatment or, where appropriate, the residence time of the reactants during the basic treatment is generally greater than or equal to 0.1 s, preferably greater than or equal to 0.3 s and with particular preference greater than or equal to 0.4 s. This duration or this residence time is commonly less than or equal to 2 h, more especially less than or equal to 1 h. The residence time of the reactants is defined as the ratio between the volume of the reactor occupied by the liquid phase or phases and the cumulative flow rate of the reactants.

The basic dehydrochlorination treatment according to the invention is generally carried out at a temperature of at least 0° C. Often this temperature is at least 20° C. Preferably it is at least 30° C. In the process for preparing the epoxide according to the invention, the reaction is generally carried out at a temperature of not more than 140° C. Preferably it is not more than 120° C. In a first particular variant the temperature is from 25 to 50° C. In a second particular variant the temperature is from 50 to 90° C.

In the process for preparing the epoxide according to the invention, the dehydrochlorination is generally carried out at a pressure of at least 0.08 bar absolute. Often this pressure is at least 0.1 bar absolute. Preferably it is at least 0.2 bar absolute. In the process for preparing the epoxide according to the invention, the dehydrochlorination is generally carried out at a pressure of not more than 25 bar absolute. Preferably it is not more than 6 bar absolute. In a first particular variant the pressure is from 0.4 to 0.8 bar absolute. In a second particular variant the pressure is from 1 to 3 bar.

The epoxide which is formed in the process for dehydrochlorinating the chlorohydrin may be removed at the rate at which it is formed, by means of distillation or stripping. Stripping may be carried out using any gas which is inert towards the epoxide. Preference is given to carrying out this stripping with steam.

Following basic treatment, the halogenated ketone content of the epoxide is commonly less than or equal to 0.01% by weight, preferably less than or equal to 0.005% by weight and with very particular preference less than or equal to 0.003% by weight. Often the epoxide contains at least 0.0001% by weight of halogenated ketones.

The invention therefore likewise provides an epoxide whose halogenated ketone content is less than or equal to 0.01% by weight. When the epoxide is epichlorohydrin its purity is preferably greater than or equal to 999 g/kg.

Without wishing to be tied by any one theory, it is thought that the reactivities of the chlorohydrin, the halogenated ketones and the epoxide are such that it is possible to remove the halogenated ketones without adversely affecting the yield of epoxide by judiciously selecting the conditions for dehydrochlorinating the chlorohydrin.

According to a second variant of the process according to the invention, the treatment intended to remove at least part of the halogenated ketones comprises a distillation, evaporation and/or stripping in the presence of water, this treatment being carried out prior to the dehydrochlorination and enabling the removal of a fraction composed essentially of water and halogenated ketones and the recovery of the chlorohydrin having a reduced halogenated ketone content.

Following this treatment, the halogenated ketone content of the chlorohydrin is commonly less than or equal to 0.1% by weight relative to the mixture of isomers of the chlorohydrin, preferably less than or equal to 0.04% by weight and with very particular preference less than or equal to 0.005% by weight. Often the chlorohydrin contains at least 0.0001% by weight of halogenated ketones relative to the mixture of isomers of the chlorohydrin.

This treatment is preferably an azeotropic distillation in the presence of water. The reason for this is that it has been found that, when the halogenated ketone is chloroacetone, for example, the water and the chloroacetone form a low-point binary azeotropic mixture, whose composition can be characterized by its boiling temperature, which is 92° C. at 1013 mbar. This composition is constituted, at this temperature and pressure, by 28% by weight of water and 72% by weight of chloroacetone. Two liquid phases separate after condensation at 25° C.; the denser, organic phase contains 95% by weight of chloroacetone and 5% by weight of water, while the aqueous phase contains 5% by weight of chloroacetone and 95% by weight of water. It has been found that the exploitation of the properties of liquid/vapour equilibria of the binary water/chloroacetone composition make it possible to remove the chloroacetone from dichloropropanol. The water required for the azeotropic distillation may originate, for example, from a process for synthesizing the dichloropropanol, in particular by chlorination of glycerol, or may be conveyed into the process subsequently.

The invention hence also provides an azeotropic composition comprising water and chloroacetone.

FIG. 1 shows a first particular scheme of plant which can be used to conduct the process for preparing an epoxide according to the invention.

A distillation column (3) is supplied via line (1) with the chlorohydrin. Water is added to the chlorohydrin via line (2). A stream which contains water and the majority of the halogenated ketones is withdrawn continuously from column (3) via line (4). The residue of the column, containing the purified chlorohydrin, is withdrawn via line (5). A basic compound is added to the residue of column (3) via line (6) and the mixture obtained supplies a reactor, which can optionally serve as a distillation column (8), via line (7). Steam is introduced into the bottom of the reactor (8) via line (9). A gas stream is withdrawn continuously from reactor (8) via line (10) and supplies a condenser (12). A liquid stream is withdrawn continuously from reactor (8) via line (11). The condensed stream (13) supplies a phase separator (14). The aqueous phase separated off is returned to the top of reactor (8) by the pipeline (15) in order to ensure reflux. The crude epoxide product constitutes the organic phase separated off, which is withdrawn by the pipeline (16). This crude epoxide is purified in a distillation sector.

In a first particular aspect of the process according to the invention, chlorohydrin is employed which contains at least a part of the chlorohydrin obtained from a preparation, starting from a polyhydroxylated aliphatic hydrocarbon, by reaction with a chlorinating agent. In this aspect the part of the chlorohydrin obtained from a preparation starting from the polyhydroxylated aliphatic hydrocarbon by reaction with a chlorinating agent makes up in general at least 1% by weight relative to the total weight of the chlorohydrin, preferably at least 5% by weight and more particularly at least 35% by weight. In this particular aspect this fraction is generally not more than 99% by weight and preferably not more than 60% by weight. The extra chlorohydrin, which can be obtained from any one of the other processes for preparing the chlorohydrin that have been envisaged above, is generally at least 1% by weight, preferably at least 5% by weight and more particularly at least 35% by weight. This fraction is not more than 99% by weight and preferably not more than 60% by weight. Among these other processes for preparing the chlorohydrin, preference is given to the hypochlorination of an olefin.

The invention accordingly further provides a first process for preparing an epoxide, comprising:
(a) a step of preparing a chlorohydrin by hypochlorinating an olefin,
(b) a step of preparing the chlorohydrin by chlorinating a polyhydroxylated aliphatic hydrocarbon, which is carried out in parallel with step (a), and
(c) a common dehydrochlorination step in which the chlorohydrin obtained in steps (a) and (b) is employed.

Preferably this first process for preparing the epoxide comprises a step of treatment intended to remove at least part of the halogenated ketones formed in the process.

According to a first embodiment of the first process for preparing the epoxide according to the invention, a mixture of the chlorohydrin obtained in steps (a) and (b) is employed in step (c).

Figure 2:
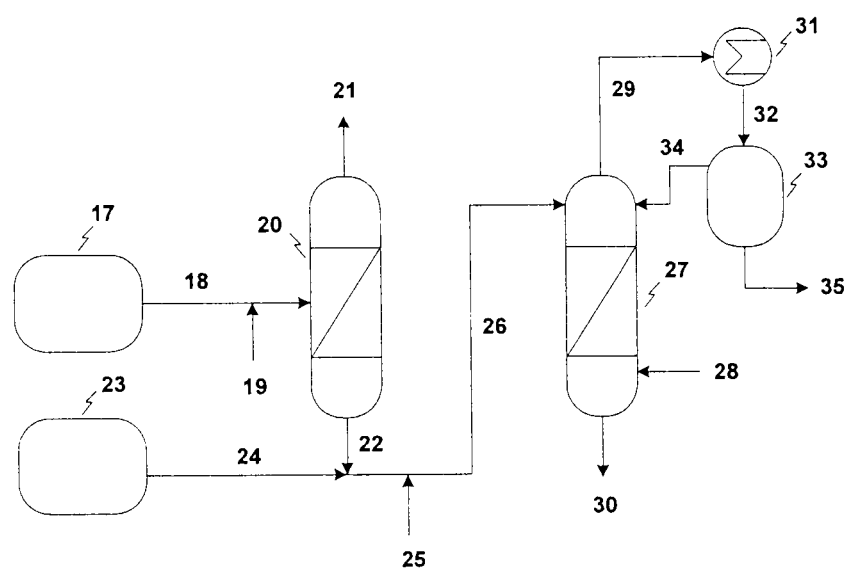

FIG. 2 shows a second particular scheme of plant which can be used to conduct the process for preparing an epoxide according to this embodiment.

A distillation column (20) is supplied via line (18) with the chlorohydrin originating from a reactor for chlorinating a polyhydroxylated aliphatic hydrocarbon (17). Water is added to the chlorohydrin via line (19). A stream which contains water and halogenated ketones is withdrawn continuously from column (20) via line (21). The residue of the column is withdrawn via line (22) and is mixed with a stream of the chlorohydrin (24) obtained from a reactor for hypochlorinating an olefin (23). A basic compound is added to the mixed stream of the chlorohydrin via line (25), and the mixture obtained supplies a reactor, which can optionally serve as distillation column (27), via line (26). Steam is introduced into the bottom of the reactor (27) via line (28). A gas stream is withdrawn continuously from reactor (27) via line (29) and supplies a condenser (31). A liquid stream is withdrawn continuously from reactor (27) via line (30). The condensed stream (32) supplies a phase separator (33). The aqueous phase separated off is returned to the top of reactor (27) by the pipeline (34), in order to ensure reflux. The crude oxide product constitutes the organic phase separated off, which is withdrawn by the pipeline (35). This crude epoxide is purified in a distillation sector.

According to a second embodiment of the first process for preparing the epoxide according to the invention, the chlorohydrin obtained in step (a) or in step (b) is employed alternatively or simultaneously in step (c).

The invention likewise provides plant for preparing an epoxide, comprising:
(a) a reactor for hypochlorinating an olefin, from which exits a reaction mixture containing a chlorohydrin, (b) a reactor for chlorinating a polyhydroxylated aliphatic hydrocarbon, from which exits a reaction mixture containing the chlorohydrin, and (c) a reactor for dehydrochlorinating which is supplied with the reaction mixtures produced from reactor (a) and from reactor (b).

This plant for preparing an epoxide preferably comprises a reactor for the treatment of removing at least part of the halogenated ketones formed in the plant.

The conditions of step (b) may be those described in application WO 2005/054167 of SOLVAY SA and in application EP 05104321.4, filed in the name of SOLVAY SA on 20 May 2005. The conditions of step (c) are, for example, as described earlier on above in the present application.

Figure 3:
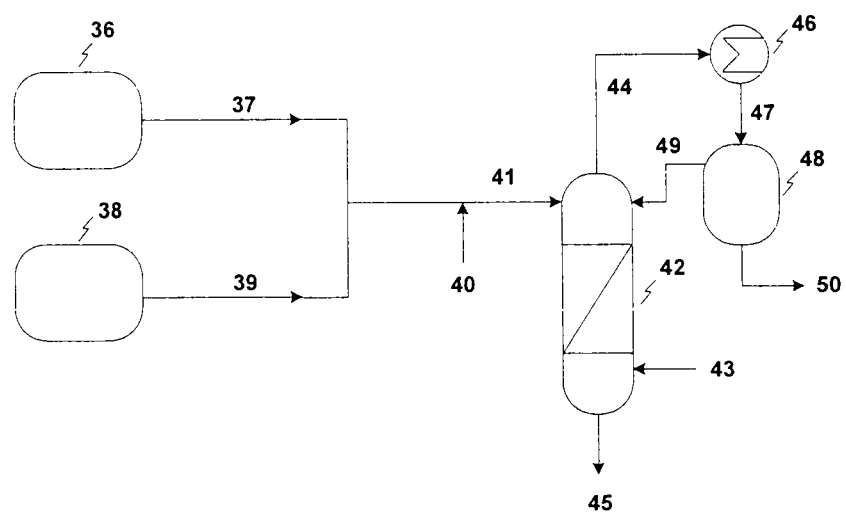

FIG. 3 shows a third particular scheme of plant which can be used to conduct the process for preparing an epoxide according to the invention.

A stream of chlorohydrin (37) coming from a reactor for chlorinating a polyhydroxylated aliphatic hydrocarbon (36) is mixed with a stream of the chlorohydrin (39) obtained from a reactor for hypochlorinating an olefin (38). A basic compound is added to the mixed stream of the chlorohydrin via line (40), and the mixture obtained supplies a reactor, which can optionally serve as distillation column (42), via line (41). Steam is introduced into the bottom of the reactor (42) via line (43). A gas stream is withdrawn continuously from reactor (42) via line (44) and supplies a condenser (46). A liquid stream is withdrawn continuously from reactor (42) via line (45). The condensed stream (47) supplies a phase separator (48). The aqueous phase separated off is returned to the top of reactor (42) by the pipeline (49), in order to ensure reflux. The crude oxide product constitutes the organic phase separated off, which is withdrawn by the pipeline (50). This crude epoxide is purified in a distillation sector.

In a second particular aspect of the process according to the invention, epoxide is obtained at least part of which has come from the separate preparation of the epoxide starting from a chlorohydrin obtained by reacting a polyhydroxylated aliphatic hydrocarbon with a chlorinating agent. In this aspect, the part of the chlorohydrin obtained from the preparation starting from the chlorinated aliphatic hydrocarbon by reaction with a chlorinating agent makes up generally at least 1% by weight relative to the total weight of the epoxide, preferably at least 5% by weight and more particularly at least 35% by weight. In this particular aspect this fraction is generally not more than 99% by weight and preferably not more than 60% by weight. The extra epoxide may have come from any one of the other processes for preparing the chlorohydrin that were envisaged above and is generally at least 1% by weight, preferably at least 5% by weight and more particularly at least 35% by weight. This fraction is not more than 99% by weight and preferably not more than 60% by weight.

Among these other processes for preparing the chlorohydrin, preference is given to hypochlorinating an olefin.

The invention hence additionally provides a second process for preparing an epoxide, comprising:

(a) a step of preparing a chlorohydrin by hypochlorinating an olefin,
(b) a step of dehydrochlorinating the chlorohydrin obtained in step (a) to give the epoxide in a dehydrochlorination reaction mixture,
(c) a step of preparing the chlorohydrin by chlorinating a polyhydroxylated aliphatic hydrocarbon,
(d) a step of dehydrochlorinating the chlorohydrin obtained in step (c) to give the epoxide in a dehydrochlorination reaction mixture, and
(e) a step of separating the epoxide from the dehydrochlorination reaction mixtures, in which the dehydrochlorination reaction mixture containing the epoxide, obtained in steps (b) and (d), is employed, and wherein step (b) is consecutive to step (a), step (d) is consecutive to step (c), and the pairing consisting of steps (a) and (b) is parallel to the pairing consisting of steps (c) and (d).

Preferably this second process for preparing an epoxide comprises a step of treatment intended to remove at least part of the halogenated ketones formed in the process.

According to a first embodiment of the second process for preparing the epoxide according to the invention, a mixture of the epoxide obtained in steps (b) and (d) is employed in step (e).

According to a second embodiment of the second process for preparing the epoxide according to the invention, the epoxide obtained in step (b) or in step (d) is employed alternatively or simultaneously in step (e).

The invention likewise provides plant for preparing an epoxide, comprising:

(a) a reactor for hypochlorinating an olefin, from which exits a reaction mixture containing a chlorohydrin,
(b) a reactor for dehydrochlorinating which is supplied with the reaction mixture produced from reactor (a), and from which exits a reaction mixture containing the epoxide,
(c) a reactor for chlorinating a polyhydroxylated aliphatic hydrocarbon, from which exits a reaction mixture containing the chlorohydrin,
(d) a reactor for dehydrochlorinating, which is supplied with the reaction mixture produced from reactor (b), and which produces a reaction mixture containing the epoxide, and
(e) a separator which is supplied with the reaction mixtures exiting from reactor (b) and from reactor (d), and in which reactor (b) is consecutive to reactor (a), reactor (d) is consecutive to reactor (c), and the pairing consisting of reactors (a) and (b) is parallel with the pairing consisting of reactors (c) and (d).

This plant for preparing an epoxide preferably comprises a reactor for the treatment of removing at least part of the halogenated ketones formed in the plant.

The conditions of step (c) may be those described in application WO 2005/054167 in the name of SOLVAY SA and in application EP 05104321.4, filed in the name of SOLVAY SA on 20 May 2005. The conditions of steps (c) and (d) are, for example, those described earlier on above in the present application.

The process for preparing the epoxide according to the invention may be integrated into an overall scheme as described in the application entitled "Process for preparing an epoxide starting from a chlorohydrin", filed in the name of SOLVAY SA on the same day as the present application, and the content of which is incorporated here by reference.

Particular mention is made of a process for preparing an epoxide comprising at least a step of purification of the epoxide formed, the epoxide being at least partly prepared by a process for dehydrochlorinating a chlorohydrin, said chlorohydrin being at least partly prepared by a process of chlorinating a polyhydroxylated aliphatic hydrocarbon, an ester of a polyhydroxylated aliphatic hydrocarbon or a mixture thereof.

It has been proved that it is possible to enhance the capacity of plants for preparing epoxides from fossil raw materials in an economic way without increasing consumption of these raw materials.

Figure 4:
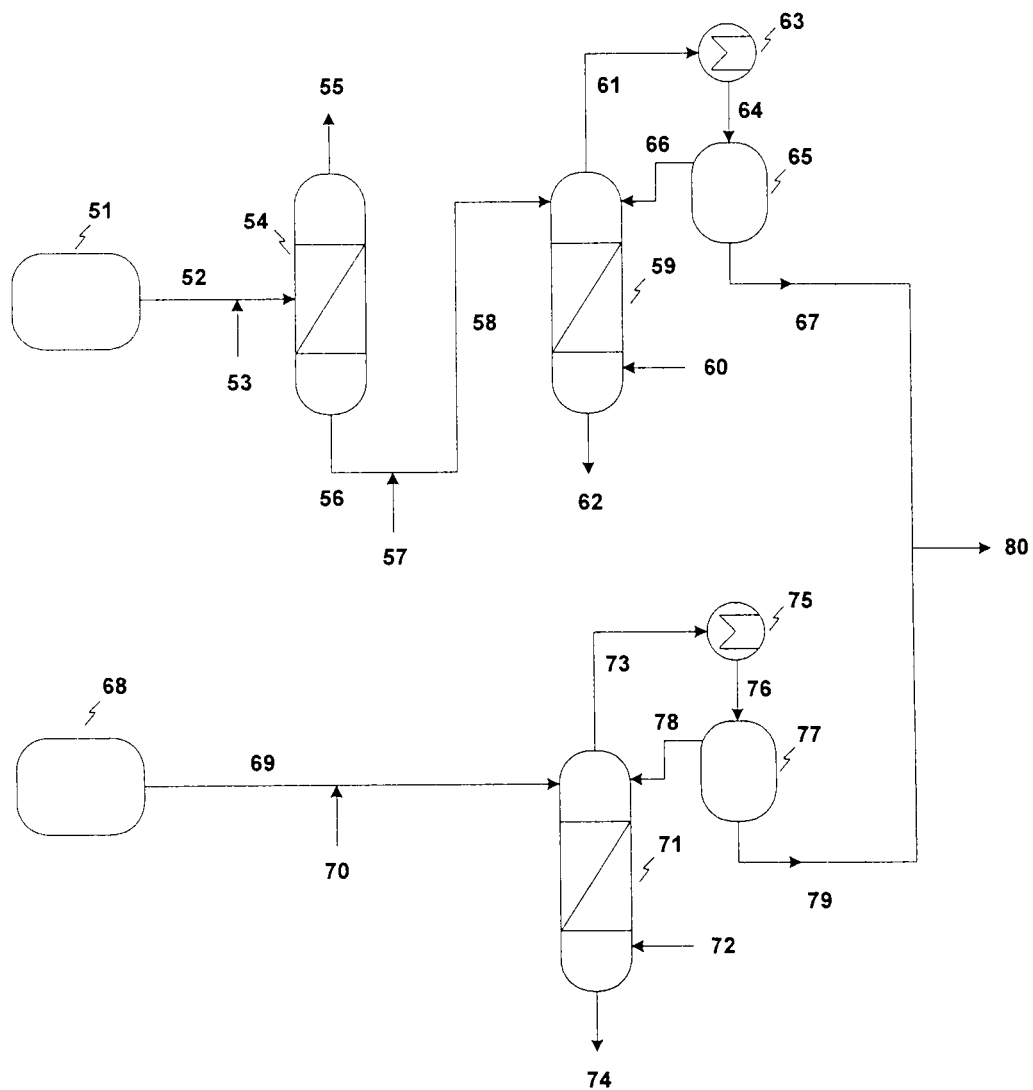

FIG. 4 shows a fourth particular scheme of plant which can be used to conduct the process for preparing an epoxide according to the invention.

A distillation column (54) is supplied with chlorohydrin originating from a reactor for chlorinating a polyhydroxylated aliphatic hydrocarbon (51) via line (52). Water is added to the chlorohydrin via line (53). A stream containing water and halogenated ketones is withdrawn continuously from column (54) via line (55). The residue of the column (54) is withdrawn via line (56). A basic compound is added to the residue of the column (54) via line (57), and the mixture obtained supplies a reactor, which can optionally serve as distillation column (59), via line (58). Steam is introduced into the bottom of reactor (59) via line (60). A gas stream is withdrawn continuously from reactor (59) via line (61) and supplies a condenser (63). A liquid stream is withdrawn continuously from reactor (59) via line (62). The condensed stream (64) supplies a phase separator (65). The aqueous phase separated off is returned to the top of reactor (59) by the pipeline (66) in order to ensure reflux. The crude epoxide product constitutes the organic phase separated off, which is withdrawn by pipeline (67).

Another reactor which can optionally serve as distillation column (71) is supplied with chlorohydrin originating from a reactor for hypochlorinating an olefin (68) via line (69), and a basic compound is added to the chlorohydrin via line (70). Steam is introduced into the bottom of reactor (71) via line (72). A gas stream is withdrawn continuously from reactor (71) via line (73) and supplies a condenser (75). A liquid stream is withdrawn continuously from reactor (71) via line (74). The condensed stream (76) supplies a phase separator (77). The aqueous phase separated off is returned to the top of reactor (71) by pipeline (78) in order to ensure reflux. The crude epoxide product constitutes the organic phase separated off, which is withdrawn by pipeline (79). The two streams of the crude epoxide are collected beforehand with a view to purification in a common distillation sector via line (80).

The processes and plant described above are preferred when the epoxide is ethylene oxide, the chlorohydrin is chloroethanol, the polyhydroxylated aliphatic hydrocarbon is ethanediol and the olefin is ethylene.

The processes and plant described above are more preferred when the epoxide is propylene oxide, the chlorohydrin is chloropropanol, the polyhydroxylated aliphatic hydrocarbon is propanediol and the olefin is propylene.

The processes and plant described above are particularly preferred when the epoxide is glycidol, the chlorohydrin is chloropropanediol, the polyhydroxylated aliphatic hydrocarbon is glycerol and the olefin is allyl chloride.

The processes and plant described above are very particularly preferred when the epoxide is epichlorohydrin, the chlorohydrin is dichloropropanol, the polyhydroxylated aliphatic hydrocarbon is glycerol and the olefin is allyl chloride.

When the epoxide is epichlorohydrin the processes and plant for preparing the epoxide may be followed by processes and plant for producing epoxy resins.

The examples below illustrate the invention, but without limiting it.

EXAMPLE 1

84 g of concentrated aqueous sodium hydroxide solution at 50% by weight (1.05 mol) are added to a solution of 129 g of 1,3-dichloropropan-2-ol in 950 ml of water. The dichloropropanol contains 3 g/kg of chloroacetone. After 1 minute of reaction at ambient temperature the conversion of the 1,3-dichloropropan-2-ol is complete, the selectivity for epichlorohydrin is 99.9% and the relative chloroacetone content relative to the epichlorohydrin produced is reduced to 11 mg/kg. The selectivity for products of hydrolysis of epichlorohydrin is 0.1%.

EXAMPLE 2

A mixture of 434.6 g of 1,3-dichloropropan-2-ol containing 3.7 g/kg of chloroacetone was distilled following addition of 66.5 g of water.

The distillation was carried out under atmospheric pressure by means of an adiabatic plate column surmounted by a device allowing a part of the vapour phase to flow back at the top of the column. The reflux ratio at the top of the column was set at 57%.

The results table below describes the composition of the various fractions collected:

| Fraction | Temperature at head of column ° C. | Mass g | Chloroacetone g/kg | 1,3-Dichloropropan-2-ol g/kg | Water g/kg |
|---|---|---|---|---|---|
| Starting mixture | | 488.7 | 3.2 | 864.2 | 132.6 |
| Distilled fraction 1 | 94 | 1.77 | 56 | 181 | 762 |
| Distilled fraction 2 | 99 | 3.54 | 32 | 231 | 737 |
| Distilled fraction 3 | 99 | 3.33 | 25 | 241 | 734 |
| Distilled fraction 4 | 98 | 7.87 | 23 | 283 | 695 |
| Distilled fraction 5 | 95 | 11.62 | 26 | 261 | 713 |
| Distilled fraction 6 | 97 | 12.3 | 25 | 227 | 749 |
| Residue in boiler | | 433.80 | 1 | 927 | 72 |

40.43 g of distillate were harvested in 6 fractions, and each distillate fraction was biphase. The concentrations given in the table relate to the sum of the two phases. This distillation made it possible to remove 60% of the chloroacetone initially present, with a total loss limited to 1.8% of 1,3-dichloropropan-2-ol in the distillates.

The invention claimed is:

1. A mixture of compounds comprising 1,3-dichloropropan-2-ol, 2,3-dichloropropan-1-ol, and a halogenated ketone, wherein the halogenated ketone content of said mixture is at least 0.0001% by weight and less than or equal to 0.1% by weight relative to the 1,3-dichloropropan-2-ol and 2,3-dichloropropan-1-ol.

2. The mixture of compounds according claim 1, whose halogenated ketone content is of less than or equal to 0.04% by weight.

3. The mixture of compounds according claim 1, whose halogenated ketone content is of less than or equal to 0.005% by weight.

4. The mixture of compounds according to claim 1, wherein the halogenated ketone contains 3 to 18 carbon atoms and in which one or more hydrogen atoms have been replaced by a halogen atom.

5. The mixture of compounds according to claim 4, wherein the halogenated ketone is a chlorinated ketone.

6. The mixture of compounds according to claim 5, wherein the chlorinated ketone is chloroacetone.

7. The mixture of compounds according to claim 1, containing more than 50% by weight of 1,3-dichloropropan-2-ol and 2,3-dichloropropan-1-ol.

8. The mixture of compounds according to claim 1, containing more than 50% by weight of 1,3-dichloropropan-2-ol and 2,3-dichloropropan-1-ol and wherein the halogenated ketone is chloroacetone.

9. The mixture of compounds according to claim 1, further comprising water.

10. The mixture of compounds according to claim 1, wherein the mass ratio between 1,3-dichloropropan-2-ol and 2,3-dichloropropan-1-ol is greater than or equal to 0.4.

11. A process for preparing the mixture of compounds according to claim 1, by hydrochlorinating glycerol, wherein during the process a halogenated ketone is formed as a by-product and which comprises at least one treatment to remove at least part of the halogenated ketone formed.

12. The process according to claim 11, wherein the glycerol is obtained starting from renewable raw materials.

13. The process according to claim 11, wherein the glycerol is obtained during the production of biodiesel or during conversions of animal or vegetable oils and fats, the conversions being selected from saponification, transesterification and hydrolysis reactions.

14. The process according to claim 13, wherein the transesterification reaction is performed in the presence of a heterogeneous catalyst.

15. The process according to claim 11, wherein the treatment to remove at least part of the halogenated ketone comprises a distillation, evaporation and/or stripping, in the presence of water, enabling the removal of a fraction composed essentially of water and halogenated ketone and the recovery of the mixture of compounds having a reduced halogenated ketone content.

16. The process according to claim 15, wherein the treatment to remove at least part of the halogenated ketones is an azeotropic distillation in the presence of water.

17. The process according to claim 16, wherein the halogenated ketone is chloroacetone.

\* \* \* \* \*